US007262340B2

(12) United States Patent
Thomas et al.

(10) Patent No.: US 7,262,340 B2
(45) Date of Patent: Aug. 28, 2007

(54) GIBBERELLIN 2-OXIDASE

(75) Inventors: Stephen Gregory Thomas, Harpenden (GB); Peter Hedden, Harpenden (GB); Andrew Leonard Phillips, Harpenden (GB)

(73) Assignee: Rothamsted Research Limited, Harpenden (GB)

( * ) Notice: Subject to any disclaimer, the term of this patent is extended or adjusted under 35 U.S.C. 154(b) by 234 days.

(21) Appl. No.: 10/670,454

(22) Filed: Sep. 26, 2003

(65) Prior Publication Data

US 2004/0229357 A1 Nov. 18, 2004

Related U.S. Application Data

(63) Continuation of application No. 09/719,108, filed as application No. PCT/GB99/01857 on Jun. 11, 1999, now Pat. No. 6,670,527.

(30) Foreign Application Priority Data

Jun. 12, 1998 (GB) ................................. 9812821.8
Jul. 15, 1998 (GB) ................................. 9815404.0

(51) Int. Cl.
*C12N 15/82* (2006.01)
*C12N 5/04* (2006.01)
*A01H 5/00* (2006.01)
*A01H 5/10* (2006.01)

(52) U.S. Cl. ........................ 800/298; 800/290; 435/419
(58) Field of Classification Search ................ 435/419, 435/468; 800/298, 290, 278, 287; 536/23.1, 536/23.6
See application file for complete search history.

(56) References Cited

FOREIGN PATENT DOCUMENTS

JP            9000069        1/1997

OTHER PUBLICATIONS

Thomas et al (1999, PNAS 96:4698-4703).*
Biemelt et al (2004, Plant Physiology 135:254-265).*
Bowie, J.U., et al., "Deciphering the Message in Protein Sequences: Tolerance to Amino Acid Substitutions," *Science* 247:1306-1310, American Association for the Advancement of Science (1990).
Chasan, R., "GA Biosynthesis: A Glimpse at the Genes," *Plant Cell* 7:141-143, American Society of Plant Physiologists (1995).
Derwent World Patents Index, Accession No. 1997-112670, English language abstract for JP 9-000069 (Document AL1).
EMBL Sequence Database, EMBL amino acid sequence from MacMillan, J., et al., "Gibberellin biosynthesis from gibberellin Al2-aldehyde in endosperm and embryos of *Marah macrocarpa*," *Plant Physiol.* 113:1369-1377 (Apr. 1997), EMBL Accession No. 004162 (submitted Jul. 1, 1997).
EMBL Sequence Database, EMBL amino acid sequence from MacMillan, J., et al., "Gibberellin biosynthesis from gibberellin Al2-aldehyde in endosperm and embryos of *Marah macrocarpa*," *Plant Physiol.* 113:1369-1377 (Apr. 1997), EMBL Accession No. Y09113 (submitted Nov. 5, 1996).
Hedden, P., and Phillips, A.L., "Gibberellin metabolism: new insights revealed by the genes," *Trends Plant Sci.* 5:523-530, Elsevier Science Ltd (Dec. 2000).
MacMillan, J., et al., "Gibberellin Biosynthesis from Gibberellin $A_{12}$-Aldehyde in Endosperm and Embryos of *Marah macrocarpus*," *Plant Physiol.* 113:1369-1377, American Society of Plant Physiologists (Apr. 1997).
McConnell, J.R., et al., "Role of *PHABULOSA* and *PHAVOLUTA* in determining radial patterning in shoots," *Nature* 411:709-713, Macmillan Magazines Ltd (Jun. 2001).
Sakamoto, T., et al., "Expression of a Gibberellin 2-Oxidase Gene Around the Shoot Apex Is Related to Phase Transition in Rice," *Plant Physiol.* 25:1508-1516, American Society of Plant Physiologists (Mar. 2001).
Singh, D.P., et al., "Gibberellins Are Required for Seed Development and Pollen Tube Growth in *Arabidopsis*," *Plant Cell* 14:3133-3147, American Society of Plant Biologists (Dec. 2002).
Thomas, S.G., et al., "Molecular cloning and functional expression of gibberellin 2-oxidases, multifunctional enzymes involved in gibberellin deactivation," *Proc. Natl. Acad. Sci. USA* 96:4698-4703, National Academy of Sciences (Apr. 1999).
Hedden, P., "Constructing dwarf rice," *Nat. Biotechnol.* 21:873-874, Nature Publishing Co. (Aug. 2003).
Sakamoto, T., et al., "Genetic manipulation of gibberellin metabolism in transgenic rice," *Nat. Biotechnol.* 21:909-913, Nature Publishing Co. (Aug. 2003).

* cited by examiner

*Primary Examiner*—Stuart F. Baum
(74) *Attorney, Agent, or Firm*—Sterne, Kessler, Goldstein & Fox P.L.L.C.

(57) ABSTRACT

A nucleic acid sequence is provided which encodes a gibberelin 2-oxidase gene which catalyzes the 2β-oxidation of a gibberelin molecule to introduce a hydroxyl group at C-2 and further catalyzes the oxidation of the hydroxyl group introduced at C-2 to yield the ketone derivative. Such sequences can find application in the preparation of transgenic plants with altered levels of gibberelin 2-oxidase.

18 Claims, 7 Drawing Sheets

```
GTTTCTCTTCCTTACCCTGTTCTGCTTCTCTTTTTCATAGTAACAATCGA
CAACAACAACAACAACCATGGTTGTTCTGTCTCAGCCAGCATTGAACCAG
TTTTTCCTTCTGAAACCATTCAAGTCCACGCCCTTGTTCACGGGGATTCC
TGTGGTCGACCTCACGCACCCCGATGCCAAGAATCTCATAGTGAACGCCT
GTAGGGACTTCGGCTTCTTCAAGCTTGTGAACCATGGTGTTCCATTGGAG
TTAATGGCCAATTTAGAAAACGAGGCCCTCAGGTTCTTTAAAAAATCTCA
GTCCGAGAAAGACAGAGCTGGTCCCCCCGACCCTTTCGGCTATGGTAGCA
AGAGGATTGGCCCAAACGGTGATGTCGGTTGGGTCGAATACCTCCTCCTC
AACACCAACCCTGATGTTATCTCACCCAAATCACTTTGCATTTTCCGAGA
AAATCCTCATCATTTCAGGGCGGTGGTGGAGAACTACATTACAGCAGTGA
AGAACATGTGCTATGCGGTGTTGGAATTGATGGCGGAGGGGTTGGGGATA
AGGCAGAGGAATACGTTAAGCAGGTTGCTGAAGGATGAGAAAAGTGATTC
GTGCTTCAGGTTGAACCACTACCCGCCTTGCCCTGAGGTGCAAGCACTGA
ACCGGAATTTGGTTGGGTTTGGGGAGCACACAGACCCACAGATAATTTCT
GTCTTAAGATCTAACAGCACATCTGGCTTGCAAATCTGTCTCACAGATGG
CACTTGGGTTTCAGTCCCACCTGATCAGACTTCCTTTTTCATCAATGTTG
GTGACGCTCTACAGGTAATGACTAATGGGAGGTTTAAAAGTGTAAAGCAT
AGGGTTTTGGCTGACACAACGAAGTCAAGGTTATCAATGATCTACTTTGG
AGGACCAGCGTTGAGTGAAAATATAGCACCTTTACCTTCAGTGATGTTAA
AAGGAGAGGAGTGTTTGTACAAAGAGTTCACATGGTGTGAATACAAGAAG
GCTGCGTACACTTCAAGGCTAGCTGATAATAGGCTTGCCCCTTTCCAGAA
ATCTGCTGCTGATTAACCAAACACACCCTTCAAATTCCACTCATTTTACG
CACGTGTTATTACCCCAATTTTCTTTCCTTTTTCTTTTCCTGTGTCTGTC
TAGGTTTCAAACAGTTGACTCTACTTGACATATATAGAAAATGAATAGGT
TAAGATGTTTATCATTTTCTTTTTCTTGTTTCATCTAAGTGTAACAGTTG
GTCTCAACTTCCCTTTCCTCAATTGTCAATGGAACGCAACTCTAGTTACA
AAAAAAAAAAAAAAAAAA
```

FIG. 1

MVVLSQPALNQFFLLKPFKSTPLFTGIPVVDLTHPDAKNLIVNACRDFGF
FKLVNHGVPLELMANLENEALRFFKKSQSEKDRAGPPDPFGYGSKRIGPN
GDVGWVEYLLLNTNPDVISPKSLCIFRENPHHFRAVVENYITAVKNMCYA
VLELMAEGLGIRQRNTLSRLLKDEKSDSCFRLNHYPPCPEVQALNRNLVG
FGEHTDPQIISVLRSNSTSGLQICLTDGTWVSVPPDQTSFFINVGDALQV
MTNGRFKSVKHRVLADTTKSRLSMIYFGGPALSENIAPLPSVMLKGEECL
YKEFTWCEYKKAAYTSRLADNRLAPFQKSAA

FIG. 2

TAATCACTATCCACCATGTCCTCTTAGCAATAAGAAAACCAATGGTGGTA
AGAATGTGATTGGTTTTGGTGAACACACAGATCCTCAAATCATCTCTGTC
TTAAGATCTAACAACACTTCTGGTCTCCAAATTAATCTAAATGATGGCTC
ATGGATCTCTGTCCCTCCCGATCACACTTCCTTCTTCTTCAACGTGGGTG
ACTCTCTCCA

FIG. 3a

GGTTATGACTAACGGGAGGTTCAAGAGTGTTAAACACAGGGTCTTAGCCG
ATACAAGGAGATCGAGGATTTCAATGATATATTTCGGCGGACCGCCATTG
AGCCAGAAGATCGCACCATTGCCATGCCTTGTCCCTGAGCAAGATGATTG
GCTTTACAAAGAATTCACTTGGTCTCAATACAAATCTTCTGCTTACAAG

FIG. 3b

```
TCAAAATCAAAAAAATTCTATCAAACAAGGAAATATATCAATGGCGGTAT
TGTCTAAACCGGTAGCAATACCAAAATCCGGGTTCTCTCTAATCCCGGTT
ATAGATATGTCTGACCCAGAATCCAAACATGCCCTCGTGAAAGCATGCGA
AGACTTCGGCTTCTTCAAGGTGATCAACCATGGCGTTTCCGCAGAGCTAG
TCTCTGTTTTAGAACACGAGACCGTCGATTTCTTCTCGTTGCCCAAGTCA
GAGAAACCCAAGTCGCAGGTTATCCCTTCGGATACGGGAACAGTAAGAT
TGGTCGGAATGGTGACGTGGGTTGGGTTGAGTACTTGTTGATGAACGCTA
ATCATGATTCCGGTTCGGGTCCACTATTTCCAAGTCTTCTCAAAAGCCCG
GGAACTTTCAGAAACGCATTGGAAGAGTACACAACATCAGTGAGAAAAAT
GACATTCGATGTTTTGGAGAAGATCACAGATGGGCTAGGGATCAAACCGA
GGAACACACTTAGCAAGCTTGTGTCTGACCAAAACACGGACTCGATATTG
AGACTTAATCACTATCCACCATGTCCTCTTAGCAATAAGAAAACCAATGG
TGGTAAGAATGTGATTGGTTTTGGTGAACACACAGATCCTCAAATCATCT
CTGTCTTAAGATCTAACAACACTTCTGGTCTCCAAATTAATCTAAATGAT
GGCTCATGGATCTCTGTCCCTCCCGATCACACTTCCTTCTTCTTCAACGT
TGGTGACTCTCTCCAGGTGATGACAAATGGGAGGTTCAAGAGCGTGAGGC
ATAGGGTTTTAGCTAACTGTAAAAAATCTAGGGTTTCTATGATTTACTTC
GCTGGACCTTCATTGACTCAGAGAATCGCTCCGTTGACATGTTTGATAGA
CAATGAGGACGAGAGGTTGTACGAGGAGTTTACTTGGTCTGAATACAAAA
ACTCTACCTACAACTCTAGATTGTCTGATAATAGGCTTCAACAATTCGAA
AGGAAGACTATAAAAAATCTCCTAAATTGATGTGATATATCTATTTAATC
TATAAGTGTGTGCTACATACAGACAATGCATCTGTATATTTTGAAGTATA
ATGTTATTTGTTAATCCAATAACTGTAAAAACATGCAAGAGTGTGTTTGT
TTGTTTCGTAATATCAACATCGCTCCCATCTTTTATGGATAAAAAAAAAA
AAAAAAAAAAACACTGTTTTGATGTAAGCTACATTTTACTTTA-GTGTACA
TCTTATTGTGTTAA-TAAATTATTTCAAAATAAAAAAAAAAAAAAAAAAA
AAAAAAAAAAAAAAAAAA
```

FIG. 5

```
MAVLSKPVAIPKSGFSLIPVIDMSDPESKHALVKACEDFGFFKVINHGVS
AELVSVLEHETVDFFSLPKSEKTQVAGYPFGYGNSKIGRNGDVGWVEYLL
MNANHDSGSGPLFPSLLKSPGTFRNALEEYTTSVRKMTFDVLEKITDGLG
IKPRNTLSKLVSDQNTDSILRLNHYPPCPLSNKKTNGGKNVIGFGEHTDP
QIISVLRSNNTSGLQINLNDGSWISVPPDHTSFFFNVGDSLQVMTNGRFK
SVRHRVLANCKKSRVSMIYFAGPSLTQRIAPLTCLIDNEDERLYEEFTWS
EYKNSTYNSRLSDNRLQQFERKTIKNLLN
```

FIG. 6

```
GAATTCGGCACGAGTTTCCTTCTTCTTCCTCAACCTTTGCTTCAATCTTC
AACAACTTTCTTTTTATAAAGATTTTGCAAGTTAAGTGTAAACCTACAAA
AACCAAACATGGTGGTTTTGCCACAGCCAGTCACTTTAGATAACCACATC
TCCCTAATCCCCACATACAAACCGGTTCCGGTTCTCACTTCCCATTCAAT
CCCCGTCGTCAACCTAGCCGATCCGGAAGCGAAAACCCGAATCGTAAAAG
CCTGCGAGGAGTTCGGGTTCTTCAAGGTCGTAAACCACGGAGTCCGACCC
GAACTCATGACTCGGTTAGAGCAGGAGGCTATTGGCTTCTTCGGCTTGCC
TCAGTCTCTTAAAAACCGGGCCGGTCCACCTGAACCGTACGGTTATGGTA
ATAAACGGATTGGACCAAACGGTGACGTTGGTTGGATTGAGTATCTCCTC
CTCAATGCTAATCCTCAGCTCTCCTCTCCTAAAACCTCCGCCGTTTTCCG
TCAAACCCCTCAAATTTTCCGTGAGTCGGTGGAGGAGTACATGAAGGAGA
TTAAGGAAGTGTCGTACAAGGTGTTGGAGATGGTTGCCGAAGAACTAGGG
ATAGAGCCAAGGGACACTCTGAGTAAAATGCTGAGAGATGAGAAGAGTGA
CTCGTGCCTGAGACTAAACCATTATCCGGCGGCGGAGGAAGAGGCGGAGA
AGATGGTGAAGGTGGGGTTTGGGGAACACACAGACCCACAGATAATCTCA
GTGCTAAGATCTAATAACACGGCGGGTCTTCAAATCTGTGTGAAAGATGG
AAGTTGGGTCGCTGTCCCTCCTGATCACTCTTCTTTCTTCATTAATGTTG
GAGATGCTCTTCAGGTTATGACTAACGGGAGGTTCAAGAGTGTTAAACAC
AGGGTCTTAGCCGATACAAGGAGATCGAGGATTTCAATGATATATTTCGG
CGGACCGCCATTGAGCCAGAAGATCGCACCATTGCCATGCCTTGTCCCTG
AGCAAGATGATTGGCTTTACAAAGAATTCACTTGGTCTCAATACAAATCT
TCTGCTTACAAGTCTAAGCTTGGTGATTATAGACTTGGTCTCTTTGAGAA
ACAACCTCTTCTCAATCATAAAACCCTTGTATGAGAGTAGTCATGATGAT
CTTTATCATCCTTTGTACGATAGAAAGTCATAATCACAAAAAGAAGGAAA
TGGATAGTGTTTTGGATTAAAAAAAAAAAAAAAAAAAA
```

FIG. 7

```
MVVLPQPVTLDNHISLIPTYKPVPVLTSHSIPVVNLADPEAKTRIVKACE
EFGFFKVVNHGVRPELMTRLEQEAIGFFGLPQSLKNRAGPPEPYGYGNKR
IGPNGDVGWIEYLLLNANPQLSSPKTSAVFRQTPQIFRESVEEYMKEIKE
VSYKVLEMVAEELGIEPRDTLSKMLRDEKSDSCLRLNHYPAAEEEAEKMV
KVGFGEHTDPQIISVLRSNNTAGLQICVKDGSWVAVPPDHSSFFINVGDA
LQVMTNGRFKSVKHRVLADTRRSRISMIYFGGPPLSQKIAPLPCLVPEQD
DWLYKEFTWSQYKSSAYKSKLGDYRLGLFEKQPLLNHKTLV
```

FIG. 8

ATGGTAATTGTGTTACAGCCAGCCAGTTTTGATAGCAACCTCTATGTTAA
TCCAAAATGCAAACCGCGTCCGGTTTTAATCCCTGTTATAGACTTAACCG
ACTCAGATGCCAAAACCCAAATCGTCAAGGCATGTGAAGAGTTTGGGTTC
TTCAAAGTCATCAACCATGGGGTCCGACCCGATCTTTTGACTCAGTTGGA
GCAAGAAGCCATCAACTTCTTTGCTTTGCATCACTCTCTCAAAGACAAAG
CGGGTCCACCTGACCCGTTTGGTTACGGTACTAAAAGGATTGGACCCAAT
GGTGACCTTGGCTGGCTTGAGTACATTCTCCTTAATGCTAATCTTTGCCT
TGAGTCTCACAAAACCACCGCCATTTTCCGGCACACCCCTGCAATTTTCA
GAGAGGCAGTGGAAGAGTACATTAAAGAGATGAAGAGAATGTCGAGCAAA
TTTCTGGAAATGGTAGAGGAAGAGCTAAAGATAGAGCCAAAGGAGAAGCT
GAGCCGTTTGGTGAAAGTGAAAGAAAGTGATTCGTGCCTGAGAATGAACC
ATTACCCGGAGAAGGAAGAGACTCCGGTCAAGGAAGAGATTGGGTTCGGT
GAGCACACTGATCCACAGTTGATATCACTGCTCAGATCAAACGACACAGA
GGGTTTGCAAATCTGTGTCAAAGATGGAACATGGGTTGATGTTACACCTG
ATCACTCCTCTTTCTTCGTTCTTGTCGGAGATACTCTTCAGGTGATGACA
AACGGAAGATTCAAGAGTGTGAAACATAGAGTGGTGACAAATACAAAGAG
GTCAAGGATATCGATGATCTACTTCGCAGGTCCTCCTTTGAGCGAGAAGA
TTGCACCATTATCATGCCTTGTGCCAAAGCAAGATGATTGCCTTTATAAT
GAGTTTACTTGGTCTCAATACAAGTTATCTGCTTACAAAACTAAGCTTGG
TGACTATAGGCTTGGTCTCTTTGAGAAACGACCTCCATTTTCTCTATCCA
ATGTTTGA

FIG. 9

MVIVLQPASFDSNLYVNPKCKPRPVLIPVIDLTDSDAKTQIVKACEEFGF
FKVINHGVRPDLLTQLEQEAINFFALHHSLKDKAGPPDPFGYGTKRIGPN
GDLGWLEYILLNANLCLESHKTTAIFRHTPAIFREAVEEYIKEMKRMSSK
FLEMVEEELKIEPKEKLSRLVKVKESDSCLRMNHYPEKEETPVKEEIGFG
EHTDPQLISLLRSNDTEGLQICVKDGTWVDVTPDHSSFFVLVGDTLQVMT
NGRFKSVKHRVVTNTKRSRISMIYFAGPPLSEKIAPLSCLVPKQDDCLYN
EFTWSQYKLSAYKTKLGDYRLGLFEKRPPFSLSNV

GIBBERELLIN 2-OXIDASE

The present application is a continuation of U.S. application Ser. No. 09/719,108, 35 U.S.C. § 371 date May 25, 2001, now U.S. Pat. No. 6,670,527, issued Dec. 30, 2003; which is the U.S. National Phase of International Application No. PCT/GB99/01857, international application date Jun. 11, 1999, which was published in English on Dec. 22, 1999 as WO 99/66029; which claims priority to United Kingdom Application Nos. GB 9812821.8, filed Jun. 12, 1998, and GB 9815404.0, filed Jul. 15, 1998; all of which are fully incorporated by reference herein.

BACKGROUND OF THE INVENTION

1. Field of the Invention

The present invention relates to a novel enzyme involved in the control of plant growth, DNA sequences coding for the enzyme and uses of the nucleotide sequence coding for the enzyme in the production of transgenic plants with improved or altered growth characteristics.

2. Related Art

The present invention relates to a novel enzyme involved in the control of plant growth, DNA sequences coding for the enzyme and uses of the nucleotide sequence coding for the enzyme in the production of transgenic plants with improved or altered growth characteristics.

The gibberellins (GAs) are a large group of diterpenoid carboxylic acids that are present in all higher plants and some fungi. Certain members of the group function as plant hormones and are involved in many developmental processes, including seed germination, stem extension, leaf expansion, flower initiation and development, and growth of the seeds and fruit. The biologically active GAs are usually $C_{19}$ compounds containing a 19-10 lactone, a C-7 carboxylic acid and a 3β-hydroxyl group. The later stages of their biosynthesis involve the oxidative removal of C-20 and hydroxylation at C-3. Hydroxylation at the 2β position results in the production of biologically inactive products. This reaction is the most important route for GA metabolism in plants and ensures that the active hormones do not accumulate in plant tissues. The GA biosynthetic enzymes 7-oxidase, 20-oxidase, 3β-hydroxylase and 2β-hydroxylase are all 2-oxoglutarate dependent dioxygenases. These are a large group of enzymes for which 2-oxoglutarate is a co-substrate that is decarboxylated to succinate as part of the reaction (see review by Hedden, P. and Kamiya, Y., in *Annu. Rev. Plant Physiol. Plant Mol. Biol.* 48 431460 (1997)).

Chemical regulators of plant growth have been used in horticulture and agriculture for many years. Many of these compounds function by changing the GA concentration in plant tissues. For example, growth retardants inhibit the activity of enzymes involved in GA biosynthesis and thereby reduce the GA content. Such chemicals are used commonly, for example, to prevent lodging in cereals and to control the growth of ornamental and horticultural plants. Conversely, GAs may be applied to plants, such as in the application of $GA_3$ to seedless grapes to improve the size and shape of the berry, and to barley grain to improve malt production. Mixtures of $GA_4$ and $GA_7$ are applied to apples to improve fruit quality and to certain conifers to stimulate cone production. There are several problems associated with the use of growth regulators. Some of the growth retardants are highly persistent in the soil making it difficult to grow other crops following a treated crop. Others require repeated applications to maintain the required effect. It is difficult to restrict application to the target plant organs without it spreading to other organs or plants and having undesirable effects. Precise targeting of the growth-regulator application can be very labour intensive. A non-chemical option for controlling plant morphology is, thus, highly desirable.

Developing seeds often contain high concentrations of GAs and relatively large amounts of GA-biosynthetic enzymes. Mature seeds of runner bean (*Phaseolus coccineus*) contain extremely high concentrations of the 2β-hydroxy GA, $GA_8$, as its glucoside, indicating that high levels of 2β-hydroxylase activity must be present. This has been confirmed for the related species *Phaseolus vulgaris* in which there is a rapid increase in GA 2β-hydroxylase activity shortly before seeds reach full maturity (Albone et al., *Planta* 177 108-115 (1989)). 2β-Hydroxylases have been partially purified from the cotyledons of *Pisum sativum* (Smith, V. A. and MacMillan, J., *Planta* 167 9-18 (1983)) and *Phaseolus vulgaris* (Griggs et al *Phytochemistry* 30 2507-2512 (1991) and Smith, V. A. and MacMillan, J., *J. Plant Growth Regul.* 2 251-264 (1984)). These studies showed that there was evidence that, for both sources, at least two enzymes with different substrate specificities are present. Two activities from cotyledons of imbibed *P. vulgaris* were separable by cation-exchange chromatography and gel-filtration. The major activity, corresponding to an enzyme of $M_r$ 26,000 by size exclusion HPLC, hydroxylated $GA_1$ and $GA_4$ in preference to $GA_9$ and $GA_{20}$, while $GA_9$ was the preferred substrate for the second enzyme ($M_r$ 42,000). However, attempts to purify the enzyme activity to obtain N-terminal information for amino acid sequencing have proved impossible because of the low abundance of the enzyme in the plant tissues relative to other proteins and the co-purification of a contaminating lectin with the enzyme activity rendering N-terminal amino acid sequencing impossible.

The regulation of gibberellin deactivation has been examined in *Pisum sativum* (garden pea) using the sln (slender) mutation as reported in Ross et al (*The Plant Journal* 7 (3) 513-523 (1995)). The sln mutation blocks the deactivation of $GA_{20}$ which is the precursor of the bioactive $GA_1$. The results of these studies indicated that the sln gene may be a regulatory gene controlling the expression of two separate structural genes involved in GA deactivation, namely the oxidation of $GA_{20}$ to $GA_{29}$ by 2β-hydroxylation at C-2 followed by the further oxidation of the hydroxyl group to a ketone ($GA_{29}$ to $GA_{29}$ atabolite). The conversion of $GA_{29}$ to $GA_{29}$-catabolite in pea seeds was inhibited by prohexadione-calcium, an inhibitor of 2-oxoglutarate-dependent dioxygenases (Nakayama et al *Plant Cell Physiol.* 31 1183-1190 (1990)), indicating that the reaction was catalysed by an enzyme of this type. Although the slender (sin) mutation in peas was found to block both the conversion of $GA_{20}$ to $GA_{29}$ and of $GA_{29}$ to $GA_{29}$-catabolite in seeds, the inability of unlabeled GA20 to inhibit oxidation of radiolabelled $GA_{29}$, and vice versa, indicated that the steps were catalysed by separate enzymes. Furthermore, in shoot tissues, the slender mutation inhibits the 2β-hydroxylation of $GA_{20}$, but not the formation of $GA_{29}$-catabolite. These observations lead to the theory that there were two separate enzymes involved in this metabolic pathway controlling the deactivation of GA in plants (Hedden, P. and Kamiya, Y., in *Annu. Rev. Plant Physiol. Plant Mol. Biol.* 48 431460 (1997)).

BRIEF SUMMARY OF THE INVENTION

However, it has now surprisingly been found that a single enzyme can, in fact, catabolise these different reactions. The present invention represents the first reported cloning of a cDNA encoding a GA 2β-hydroxylase that acts on $C_{19}$-GAs and for which 2β-hydroxylation is its only hydroxylase activity. A cDNA clone from pumpkin seed encodes an enzyme that has both 2β- and 3β-hydroxylase activities (Lange et al. *Plant Cell* 9 1459-1467 (1997)), but its major activity is 3β-hydroxylation and it acts as a 2β-hydroxylase only with tricarboxylic acid ($C_{20}$) substrates; it does not 2β-hydroxylate $C_{19}$-GAs. Since the new enzyme of the present invention catalyses both the β-hydroxylation and further oxidation of the substituted hydroxyl group to a ketone group at C-2, the enzyme has been termed a "GA 2-oxidase".

DETAILED DESCRIPTION OF THE INVENTION

According to a first aspect of the present invention there is provided an isolated, purified or recombinant nucleic acid sequence encoding a gibberellin 2-oxidase enzyme comprising a nucleic acid sequence as shown in FIG. 1 or a functional derivative thereof, or its complementary strand or a homologous sequence thereto.

A system of nomenclature for the GA-biosynthesis genes has now been introduced (Coles et al *The Plant Journal* 17(5) 547-556 (1999). References in the present application to the gibberellin 2-oxidase gene of *Phaseolus coccineus* should be understood as also referring to PcGA2ox1. References in the present application to the gibberellin 2-oxidase genes of *Arabidopsis thaliana* as at-2bt3, at-2bt24 and T31E10.11 should be understood as also referring to AtGA2ox1, AtGA2ox2 and AtGA2ox3 respectively.

Nucleic acid sequences of the present invention which encode a gibberellin 2-oxidase (GA 2-oxidase) are 2-oxoglutarate-dependent dioxygenases that introduce a hydroxyl group at C-2β on GAs, particularly $C_{19}$-GAs, including the bioactive GAs such as $GA_1$ and $GA_4$. They may also oxidise the 2β-hydroxylated GAs further to give GA-catabolites, which have a ketone function at C-2. The lactone bridge of these catabolites may also be opened to produce a C-19 carboxylic acid and a double bond at C-10. The activity of the 2-oxidases results in inactivation of bioactive GAs or in the conversion of biosynthetic precursors of active GAs to products that cannot be converted to bioactive forms. A preferred nucleic acid sequence of the present invention therefore encodes a gibberellin 2-oxidase enzyme capable of oxidising $C_{19}$-gibberellin compounds by introduction of a hydroxyl group at C-2β. The enzyme may also oxidise the 2β-hydroxyl group to a ketone group. Preferred substrates of gibberellin 2-oxidases of the present invention are $GA_9$, $GA_4$, $GA_{20}$ and $GA_1$.

In the context of the present invention, the degree of identity between amino acid sequences may be at least 40%, suitably 50% or higher, e.g. 55%, 60%, 65%, 70%, 75%, 80%, 85%, 90% or 95%. At the nucleotide level, the degree of identity may be at least 50%, suitably 60% or higher, e.g. 65%, 70%, 75%, 80%, 85%, 90% or 95%. A homologous sequence according to the present invention may therefore have a sequence identity as described above. Sequence homology may be determined using any conveniently available protocol, for example using Clustal X™ from the University of Strasbourg and the tables of identities produced using Genedoc™ (Karl B. Nicholas).

Also included within the scope of the present invention are nucleic acid sequences which hybridises to a sequence in accordance with the first aspect of the invention under stringent conditions, or a nucleic acid sequence which is homologous to or would hybridise under stringent conditions to such a sequence but for the degeneracy of the genetic code, or an oligonucleotide sequence specific for any such sequence.

Stringent conditions of hybridisation may be characterised by low salt concentrations or high temperature conditions. For example, highly stringent conditions can be defined as being hybridisation to DNA bound to a solid support in 0.5M $NaHPO_4$, 7% sodium dodecyl sulfate (SDS), 1 mM EDTA at 65° C., and washing in 0.1×SSC/ 0.1% SDS at 68° C. (Ausubel et al eds. "*Current Protocols in Molecular Biology*" 1, page 2.10.3, published by Green Publishing Associates, Inc. and John Wiley & Sons, Inc., New York, (1989)). In some circumstances less stringent conditions may be required. As used in the present application, moderately stringent conditions can be defined as comprising washing in 0.2×SSC/0.1% SDS at 42° C. (Ausubel et al (1989) supra). Hybridisation can also be made more stringent by the addition of increasing amounts of formamide to destabilise the hybrid nucleic acid duplex. Thus particular hybridisation conditions can readily be manipulated, and will generally be selected according to the desired results. In general, convenient hybridisation temperatures in the presence of 50% formamide are 42° C. for a probe which is 95 to 100% homologous to the target DNA, 37° C. for 90 to 95% homology, and 32° C. for 70 to 90% homology.

An example of a preferred nucleic acid sequence of the present invention is one which encodes an enzyme which has the activity of a gibberellin 2-oxidase enzyme of *Phaseolus coccineus* (for example PcGA2ox1) or an equivalent protein of another member of the Fabaceae family. A nucleic acid sequence of the present invention may also encode a gibberellin 2-oxidase enzyme from *Phaseolus vulgaris* or from *Arabidopsis thaliana* (for example AtGA2ox1, AtGA2ox2 or AtGAox3).

Other nucleic acid sequences in accordance with this aspect of the present invention may also comprise a nucleic acid sequence as previously defined in which the coding sequence is operatively linked to a promoter. The promoter may be constitutive and/or specific for expression in a particular plant cell or tissue, for example in roots using tobacco RB7 (Yamamoto et al *Plant Cell* 3 371-382 (1991)); in green tissues using tomato rbcS-3A (Ueda et al *Plant Cell* 1 217-227 (1989)); in dividing cells using maize histone H3 (Brignon et al *Plant Mol. Biol.* 22 1007-1015 (1993)), or Arabidopsis CYC07 (Ito et al *Plant Mol. Biol.* 24 863-878 (1994)); in vegetable meristem using Arabidopsis KNAT1 (Lincoln et al *Plant Cell* 6 1859-1876 (1994)); in vascular tissue using bean GRP1.8 (Keller, B., & Heierli, D., *Plant Mol. Biol.* 26 747-756 (1994)); in flower using Arabidopsis ACT11 (Huang et al *Plant Mol. Biol.* 33 125-139 (1997)) or petunia chalcone synthase (Vandermeer et al *Plant Mol. Biol.* 15 95-109 (1990)); in pistil using potato SK2 (Ficker et al *Plant Mol. Biol.* 35 425-431 (1997)); in anther using *Brassica* TA29 (Deblock, M., & Debrouwer, D., *Planta* 189 218-225 (1993)); in fruit using tomato polygalacturonase (Bird et al *Plant Mol. Biol.* 11 651-662 (1988)). Alternative promoters may be derived from plant viruses, for example the Cauliflower mosaic virus $^{35}S$ promoter (CaMV). Suitable promoter sequences can include promoter sequences from plant species, for example from the family *Brassicaceae*.

The present invention therefore also extends to an isolated, purified or recombinant nucleic acid sequence comprising a promoter which naturally drives expression of a gene encoding a gibberellin 2-oxidase enzyme comprising a nucleic acid sequence as shown in FIG. 1 or a functional derivative thereof, or its complementary strand, or a sequence homologous thereto. The gibberellin 2-oxidase enzyme may be of *Phaseolus coccineus* (for example PcGA2ox1) or an equivalent protein of another member of the Fabaceae family. Such nucleic acid sequences may also encode a gibberellin 2-oxidase enzyme from *P. vulgaris* or *A. thaliana* (for example AtGA2ox1, AtGA2ox2 or AtGA2ox3). Preferably, the nucleic acid sequence comprises a promoter which drives expression of a gibberellin 2-oxidase enzyme from *P. coccineus*, *P. vulgaris* or *A. thaliana*. Such promoter sequences include promoters which occur naturally 5' to the coding sequence of the sequence shown in FIG. 1. Promoters may also be selected to constitutively overexpress the nucleic acid coding for the gibberellin 2-oxidase gene. Promoters that are induced by internal or external factors, such as chemicals, plant hormones, light or stress could be used. Examples are the pathogenesis related genes inducible by salicylic acid, copper-ontrollable gene expression (Mett et al *Proc. Nat'l. Acad. Sci. USA* 90 4567-4571 (1993)) and tetracycline-regulated gene expression (Gatz et al *Plant Journal* 2 397-404 (1992)). Examples of gibberellin-inducible genes are γ-TIP (Phillips, A. L., & Huttly, A. K., *Plant Mol. Biol.* 24 603-615 (1994)) and GAST (Jacobsen, S. E., & Olszewski, N. E., *Planta* 198 78-86 (1996)). Gibberellin 20-oxidase genes are down-regulated by GA (Phillips et al *Plant Physiol.* 108 1049-1057 (1995)) and their promoter coupled to the GA 2-oxidase ORF may also find application in this aspect of the invention.

Gibberellin 2-oxidase enzymes coded for by nucleic acid sequences of the present invention may suitably act to catalyse the 2β-oxidation of a $C_{19}$-gibberellin molecule to introduce a hydroxyl group at C-2 followed by further oxidation to yield the ketone derivative.

The nucleic acid sequences of the present invention may also code for RNA which is antisense to the RNA normally found in a plant cell or may code for RNA which is capable of cleavage of RNA normally found in a plant cell. Accordingly, the present invention also provides a nucleic acid sequence encoding a ribozyme capable of specific cleavage of RNA encoded by a gibberellin 2-oxidase gene. Such ribozyme-encoding DNA would generally be useful in inhibiting the deactivation of gibberellins, particularly $C_{19}$-GAs.

Nucleic acid sequences in accordance with the present invention may further comprise 5' signal sequences to direct expression of the expressed protein product. Such signal sequences may also include protein targeting sequences which can direct an expressed protein to a particular location inside or outside of a host cell expressing such a nucleic acid sequence. Alternatively, the nucleic acid sequence may also comprise a 3' signal such as a polyadenylation signal or other regulatory signal.

The present invention therefore offers significant advantages to agriculture in the provision of nucleic acid sequences to regulate the metabolism of the gibberellin plant hormones. The regulation could be to either inhibit plant growth by promoting the action of gibberellin 2-oxidase or to promote plant growth by preventing the deactivation of gibberellin by gibberellin 2-oxidase. For example, in 1997, there was lodging in about 15% of the wheat and 30% of the barley crop in the UK with an estimated cost to the growers of £100 m. The availability of lodging-resistant cereals with shorter, stronger stems as a result of reduced GA content could be of considerable financial benefit.

According to another aspect of the present invention there is provided an antisense nucleic acid sequence which includes a transcribable strand of DNA complementary to at least part of the strand of DNA that is naturally transcribed in a gene encoding a gibberellin 2-oxidase enzyme, such as the gibberellin 2-oxidase enzymes from *P. coccineus, P. vulgaris* or *A. thaliana*. Preferred genes according to the present invention include PcGA2ox1, AtGA2ox1, AtGA2ox2 and AtGA20×3.

The antisense nucleic acid and ribozyme-encoding nucleic acid described above are examples of a more general principle: according to a further aspect of the invention there is provided DNA which causes (for example by its expression) selective disruption of the proper expression of gibberellin 2-oxidase genes, or in preferred embodiments the *P. coccineus* gene PcGA2ox1.

According to another aspect of the present invention there is provided an isolated, purified or recombinant polypeptide comprising a gibberellin 2-oxidase enzyme having the amino acid sequence as shown in FIG. 2.

Recombinant DNA in accordance with the invention may be in the form of a vector. The vector may for example be a plasmid, cosmid, phage or artificial chromosome. Vectors will frequently include one or more selectable markers to enable selection of cells transfected (or transformed: the terms are used interchangeably in this specification) with them and, preferably, to enable selection of cells. harbouring vectors incorporating heterologous DNA. Appropriate "start" and "stop" signals will generally be present. Additionally, if the vector is intended for expression, sufficient regulatory sequences to drive expression will be present; however, DNA in accordance with the invention will generally be expressed in plant cells, and so microbial host expression would not be among the primary objectives of the invention, although it is not ruled out (such as for example in bacterial or yeast host cells). Vectors not including regulatory sequences are useful as cloning vectors.

Cloning vectors can be introduced into *E. coli* or another suitable host which facilitates their manipulation. According to another aspect of the invention, there is therefore provided a host cell transfected or transformed with a nucleic acid sequence as described above. A further embodiment of the invention is the provision of enzymes by expression of GA 2-oxidase cDNAs in heterologous hosts, such as *Escherichia coli*, yeasts including strains of *Saccharomyces cerevisiae*, or insect cells infected with a baculovirus containing recombinant DNA. The enzymes could be used for the production of 2β-hydroxylated GAs and GA-catabolites or for the preparation of antibodies raised against GA 2-oxidases. The host cell may also suitably be a plant cell in plant cell culture or as part of a callus.

Nucleic acid sequences in accordance with this invention may be prepared by any convenient method involving coupling together successive nucleotides, and/or ligating oligo- and/or poly-nucleotides, including cell-free in vitro processes, but recombinant DNA technology forms the method of choice.

Ultimately, nucleic acid sequences in accordance with the present invention will be introduced into plant cells by any suitable means. According to a still further aspect of the invention, there is provided a plant cell including a nucleic acid sequence in accordance with the invention as described above.

Preferably, nucleic acid sequences of the present invention are introduced into plant cells by transformation using the binary vector pLARS120, a modified version of pGPTV-Kan (Becker et al *Plant Mol. Biol.* 20 1195-1197 (1992)) in which the β-glucuronidase reporter gene is replaced by the Cauliflower mosaic virus 35S promoter from pBI220 (Jefferson, R. A., *Plant Mol. Biol. Rep.* 5 387405 (1987)). Such plasmids may be then introduced into *Agrobacterum tumefaciens* by electroporation and can then be transferred into the host cell via a vacuum filtration procedure. Alternatively, transformation may be achieved using a disarmed Ti-plasmid vector and carried by *Agrobacterium* by procedures known in the art, for example as described in EP-A-0116718 and EP-A-0270822. Where *Agrobacterium* is ineffective, the foreign DNA could be introduced directly into plant cells using an electrical discharge apparatus alone, such as for example in the transformation of monocotyledonous plants. Any other method that provides for the stable incorporation of the nucleic acid sequence within the nuclear DNA or mitochondrial DNA of any plant cell would also be suitable. This includes species of plant which are not yet capable of genetic transformation.

Preferably, nucleic acid sequences in accordance with the invention for introduction into host cells also contain a second chimeric gene (or "marker" gene) that enables a transformed plant containing the foreign DNA to be easily distinguished from other plants that do not contain the foreign DNA. Examples of such a marker gene include antibiotic resistance (Herrera-Estrella et al *EMBO J.* 2 987-995 (1983)), herbicide resistance (EP-A-0242246) and glucuronidase (GUS) expression (EP-A-0344029). Expression of the marker gene is preferably controlled by a second promoter which allows expression in cells at all stages of development so that the presence of the marker gene can be determined at all stages of regeneration of the plant.

A whole plant can be regenerated from a single transformed plant cell, and the invention therefore provides transgenic plants (or parts of them, such as propagating material, i.e. protoplasts, cells, calli, tissues, organs, seeds, embryos, ovules, zygotes, tubers, roots, etc.) including nucleic acid sequences in accordance with the invention as described above. In the context of the present invention, it should be noted that the term "transgenic" should not be taken to be limited in referring to an organism as defined above containing in their germ line one or more genes from another species, although many such organisms will contain such a gene or genes. Rather, the term refers more broadly to any organism whose germ line has been the subject of technical intervention by recombinant DNA technology. So, for example, an organism in whose germ line an endogenous gene has been deleted, duplicated, activated or modified is a transgenic organism for the purposes of this invention as much as an organism to whose germ line an exogenous DNA sequence has been added.

Preferred species of plants include but are not limited to monocotyledonous plants including seed and the progeny or propagules thereof, for example *Lolium, Zea, Triticum, Sorghum, Triticale, Saccharum, Bromus, Oryzae, Avena, Hordeum, Secale* and *Setaria*. Especially useful transgenic plants are maize, wheat, barley plants and seed thereof. Dicotyledenous plants are also within the scope of the present invention and preferred transgenic plants include but are not limited to the species *Fabaceae, Solanum, Brassicaceae*, especially potatoes, beans, cabbages, forest trees, roses, clematis, oilseed rape, sunflower, chrysanthemum, poinsettia and antirrhinum (snapdragon).

Screening of plant cells, tissue and plants for the presence of specific DNA sequences may be performed by Southern analysis as described in Sambrook et al (*Molecular Cloning: A Laboratory Manual*, Second edition (1989)). This screening may also be performed using the Polymerase Chain Reaction (PCR) by techniques well known in the art.

Transformation of plant cells includes separating transformed cells from those that have not been transformed. One convenient method for such separation or selection is to incorporate into the material to be inserted into the transformed cell a gene for a selection marker. As a result only those cells which have been successfully transformed will contain the marker gene. The translation product of the marker gene will then confer a phenotypic trait that will make selection possible. Usually, the phenotypic trait is the ability to survive in the presence of some chemical agent, such as an antibiotic, e.g. kanamycin, G418, paromomycin, etc, which is placed in a selection media. Some examples of genes that confer antibiotic resistance, include for example, those coding for neomycin phosphotransferase kanamycin resistance (Velten et al *EMBO J.* 3 2723-2730 (1984)), hygromycin resistance (van den Elzen et al *Plant Mol. Biol.* 5 299-392 (1985)), the kanamycin resistance (NPT II) gene derived from Tn5 (Bevan et al *Nature* 304 184-187 (1983); McBride et al *Plant Mol. Biol.* 14 (1990)) and chloramphenicol acetyltransferase. The PAT gene described in Thompson et al (*EMBO J.* 6 2519-2523 (1987)) may be used to confer herbicide resistance.

An example of a gene useful primarily as a screenable marker in tissue culture for identification of plant cells containing genetically engineered vectors is a gene that encodes an enzyme producing a chromogenic product. One example is the gene coding for production of β-glucuronidase (GUS). This enzyme is widely used and its preparation and use is described in Jefferson (*Plant Mol. Biol. Reporter* 5 387-405 (1987)).

Once the transformed plant cells have been cultured on the selection media, surviving cells are selected for further study and manipulation. Selection methods and materials are well known to those of skill in the art, allowing one to choose surviving cells with a high degree of predictability that the chosen cells will have been successfully transformed with exogenous DNA.

After transformation of the plant cell or plant using, for example, the *Agrobacterium* Ti-plasmid, those plant cells or plants transformed by the Ti-plasmid so that the enzyme is expressed, can be selected by an appropriate phenotypic marker. These phenotypic markers include, but are not limited to, antibiotic resistance. Other phenotypic markers are known in the art and may be used in this invention.

Positive clones are regenerated following procedures well-known in the art. Subsequently transformed plants are evaluated for the presence of the desired properties and/or the extent to which the desired properties are expressed. A first evaluation may include, for example, the level of bacterial/fungal resistance of the transformed plants, stable heritability of the desired properties, field trials and the like.

By way of illustration and summary, the following scheme sets out a typical process by which transgenic plant material, including whole plants, may be prepared. The process can be regarded as involving five steps:

(1) first isolating from a suitable source or synthesising by means of known processes a DNA sequence encoding a protein exhibiting GA 2-oxidase activity;

(2) operably linking the said DNA sequence in a 5' to 3' direction to plant expression sequences as defined hereinbefore;

(3) transforming the construct of step (2) into plant material by means of known processes and expressing it therein;

(4) screening of the plant material treated according to step (3) for the presence of a DNA sequence encoding a protein exhibiting gibberellin 2-oxidase activity: and (5) optionally regenerating the plant material transformed according to step (3) to a whole plant.

The present invention thus also comprises transgenic plants and the sexual and/or asexual progeny thereof, which have been transformed with a recombinant DNA sequence according to the invention. The regeneration of the-plant can proceed by any known convenient method from suitable propagating material either prepared as described above or derived from such material.

The expression "asexual or sexual progeny of transgenic plants" includes by definition according to the invention all mutants and variants obtainable by means of known process, such as for example cell fusion or mutant selection and which still exhibit the characteristic properties of the initial transformed plant, together with all crossing and fusion products of the transformed plant material.

Another object of the invention concerns the proliferation material of transgenic plants. The proliferation material of transgenic plants is defined relative to the invention as any plant material that may be propagated sexually in vivo or in vitro. Particularly preferred within the scope of the present invention are protoplasts, cells, calli, tissues, organs, seeds, embryos, egg cells, zygotes, together with any other propagating material obtained from transgenic plants.

A further aspect of the invention is the provision of an antibody raised against at least a part of the amino acid sequence of gibberellin 2-oxidase. Such antibody is useful in screening a cDNA library in suitable vectors derived from the plant tissue RNA.

The gibberellin 2-oxidase gene according to the invention is useful in the modification of growth and developmental processes in transgenic plants. Another important aspect of the present invention is therefore its use in the preparation of transgenic plants or seeds in which the gibberellin 2-oxidase is constitutively overexpressed to reduce the concentration of bioactive gibberellins (GAs) in the plants or seeds. Preferred gibberellin 2-oxidase genes include PcGA2ox1, AtGA2ox1, AtGA2ox2 and AtGA20x3. Such transgenic plants overexpressing the GA 2-oxidase would resemble plants that had been treated with growth retardants. The invention could therefore be used to reduce vegetative growth as in, for example, the prevention of lodging in cereals, including rice, and the improvement in grain yield, the prevention of lodging in oilseed rape and the improvement of canopy structure, the improvement in seedling quality for transplantation, the reduction in growth of amenity grasses, the reduction in shoot growth in orchard and ornamental trees, the production of ornamental plants with more compact growth habit, the improvement in tolerance to cold, draught and infection, the increase in yields by diversion of assimilates from vegetative to reproductive organs, the prevention of bolting in rosette plants, such as sugar beet, lettuce, brassicas and spinach. The invention may also be used to induce male and/or female sterility by expression in floral organs, to prevent pre-harvest sprouting in cereals, to reduce shoot growth in hedging plants, to inhibit reversibly the development or germination of seeds and to reduce shoot growth of commercial wood species.

Overexpression of the nucleic acid sequences encoding gibberellin 2-oxidase may be achieved using DNA constructs comprising constitutive promoters and nucleic acid coding sequences in transgenic plants prepared by recombinant DNA technology. Alternatively, the overexpression may be achieved using the technique of homologous recombination to insert into the nucleus of a cell a constitutive promoter upstream of a normally silent copy of the nucleic acid sequence of the present invention.

The present invention also provides in an additional aspect the use of a nucleic acid sequence as previously defined in the preparation of transgenic plants and/or seeds in which expression of endogenous GA 2-oxidase genes in transgenic plants is reduced (i.e. silenced), by, for example, the expression of antisense copies of the endogenous GA 2-oxidase DNA sequences, the expression of truncated sense copies of the endogenous gene (co-suppression) or the use of synthetic ribozymes targeted to the endogenous transcripts. Preferred gibberellin 2-oxidase genes according to this aspect of the invention include PcGA2ox1, AtGA2ox1, AtGA2ox2 and AtGA20x3.

This would result in plants with reduced turnover, and hence increased concentrations, of bioactive GAs. In this form, the invention could be used, for example, to improve fruit set and growth in seedless grapes, citrus and pear, improve skin texture and fruit shape in apple, increase stem length and therefore yield in sugar cane, increase yield and earliness in celery and rhubarb, improve malting yields and quality in cereals, particularly barley. It could also be used to increase growth in woody species.

Preferred features of the second and subsequent aspects of the invention are as for the first aspect *mutatis mutandis*.

BRIEF DESCRIPTION OF THE DRAWINGS

The invention will now be further described by reference to the following examples and drawings which are provided for the purpose of explanation only and should not be construed as being limiting on the present invention. In the examples, reference is made to a number of drawings in which:

FIG. 1 shows the nucleotide sequence of the *P. coccineus* 2-oxidase cDNA clone pc-2boh.dna (PcGA2ox1) (SEQ ID NO: 1) with the coding region at residues 68-1063nt (332 amino acids).

FIG. 2 shows the deduced amino acid sequence for the *P. coccineus* nucleotide sequence (PcGA2ox1) (SEQ ID NO: 2) shown in FIG. 1.

FIG. 3 shows the DNA probe sequences for *A. thaliana* probe T3 (SEQ ID NO: 3) (FIG. 3a) and probe T24 (SEQ ID NO: 4)(FIG. 3b).

FIG. 5 shows the partial nucleotide sequence for *A. thaliana* clone at-2bt3 (AtGA2ox1)(SEQ ID NO: 5) with the coding region at residues 41-1027nt (329 amino acids).

FIG. 6 shows the deduced amino acid sequence for *A. thaliana* clone at-2bt3 (AtGA2ox1)(SEQ ID NO: 6).

FIG. 7 shows the partial nucleotide sequence for *A. thaliana* clone at-2bt24 (AtGA2ox2) (SEQ ID NO: 7), with the coding region at residues 109-1131nt (341 amino acids).

FIG. 8 shows the deduced amino acid sequence for *A. thaliana* clone at2bt24 (AtGA2ox2)(SEQ ID NO: 8).

FIG. 9 shows the nucleotide sequence for *A. thaliana* genomic clone T31E10.11 (AtGA2ox3)(SEQ ID NO: 9).

FIG. 10 shows the deduced amino acid sequence for genomic clone T31E10.11 (AtGA2ox3)(SEQ ID NO: 10).

EXAMPLES

Example 1

Figure 4:
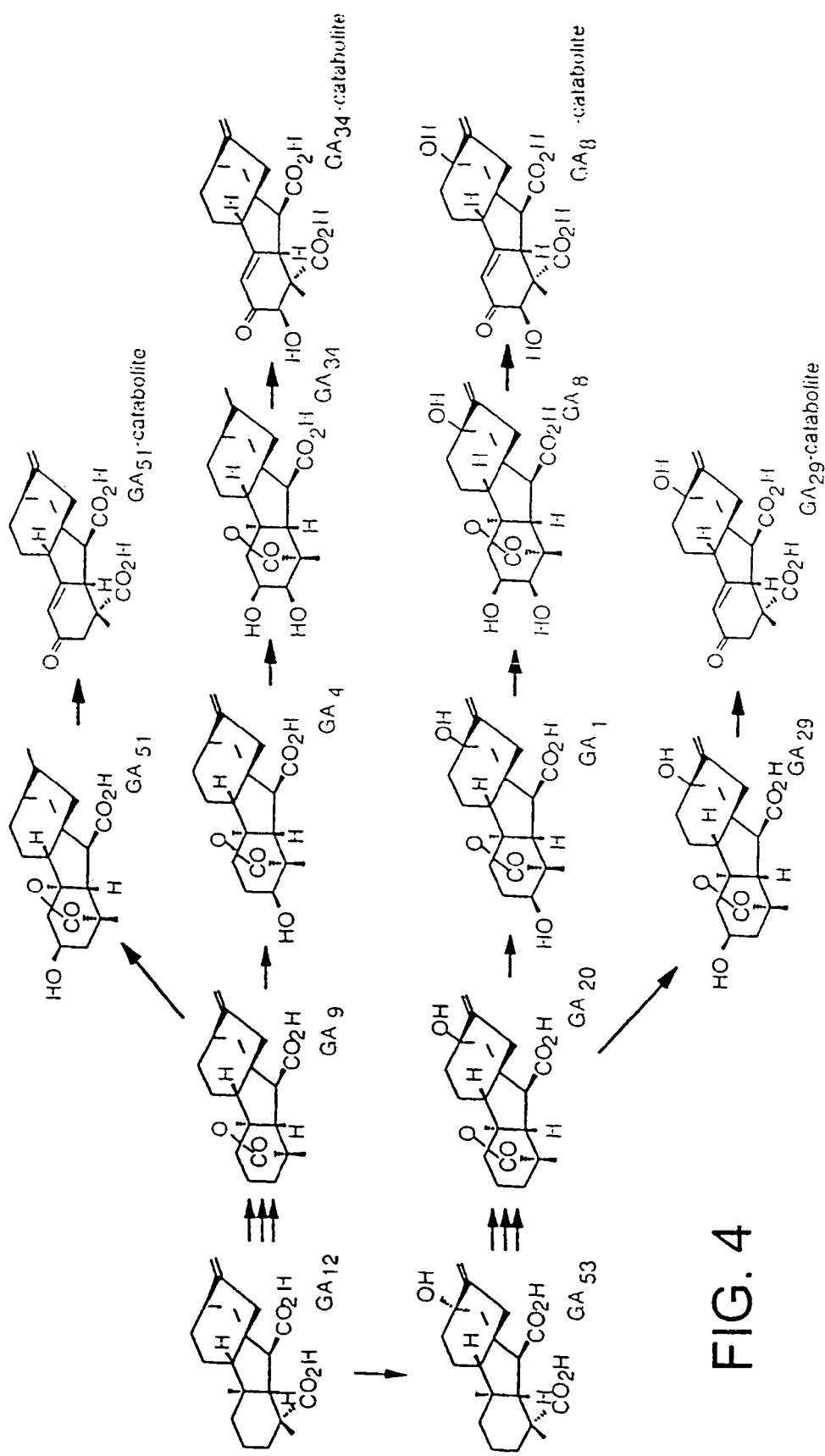
FIG. 4 shows the two major pathways of gibberellin (GA) biosynthesis.

Isolation of cDNA Clone Encoding GA 2β-hydroxylase from *Phaseolus coccineus*

A cDNA clone encoding a GA 2β-hydroxylase was isolated from *Phaseolus coccineus* embryos by screening a cDNA library for expression of functional enzyme as follows. RNA was extracted from the cotyledons of mature *Phaseolus coccineus* seeds, according to Dekker et al. (1989). Poly (A)+ mRNA was purified by chromatography on oligo(dT) cellulose. cDNA was synthesized from 5 μg of poly(A)+ mRNA using a directional cDNA synthesis kit (λ-ZAP II cDNA synthesis kit, Stratagene). The cDNA was ligated into λ-ZAP II arms, packaged using Gigapack Gold III (Stratagene) and $1\times10^6$ recombinant clones amplified according to the manufacturer's instructions.

A phagemid stock was prepared from the *Phaseolus coccineus* cDNA library ($1\times10^9$ pfu) according to the manufacturer's in vivo excision protocol (Stratagene). For the primary screen, *E. coli* SOLR were infected with the phagemid stock according to the manufacturer's instructions (Stratagene), resulting in approximately 11000 colony forming units (cfu). These were subdivided into 48 wells (6×8 array) of a micro-titre plate (well volume=3.5 ml) and amplified by overnight growth at 37° C. with shaking, in 0.5 ml of 2×YT broth supplemented with 50 μg/ml kanamycin and 100 μg/ml carbenicillin. Aliquots (20 μl) from the six wells in each row, and from the eight wells in each column were combined to make 14 pools and each added to 10 ml 2YT broth, supplemented with 50 μg/ml kanamycin and 100 μg/ml carbenicillin, and grown at 37° C. with shaking until an OD 600 nm of 0.2-0.5. The cultures were then transferred to a 30° C. shaking incubator and recombinant fusion protein production induced by the addition of IPTG to 1 mM. Cultures were induced for 16 hours. The bacteria were pelleted by centrifugation (3000 g×10 min) and resuspended in 750 μl of lysis buffer (100 mM Tris HCl pH 7.5, 5 mM DTT). Bacteria were lysed by sonication (3×10 s) and the cell debris pelleted by centrifugation for 10 min in a microfuge. The supernatants were assayed for GA 2β-hydroxylase activity as described below. Cell lysates from pooled bacteria of row 6 (R6) and column 1 (C1) were capable of catalysing the release of $^3H_2O$ from-[1,2-3$H_2$]GA$_4$ and [2,3-$^3H_2$]GA$_9$. For the secondary screen bacteria from well R6C1 were plated out on 2YT agar plates, supplemented with 100 μg./ml carbenicillin and 50 μg/ml kanamycin, and grown for 16 hours at 37° C. One hundred single colonies were picked at random and transferred to 5 ml 2×YT broth containing 100 mg/ml carbenicillin and 50 mg/ml kanamycin and grown, with shaking, for 16 hours at 37° C. The cultures were arranged in a 10×10 grid and pools from each row and column induced and tested for GA 2β-hydroxylase activity as described above. Rows 2 and 9 and columns 7 and 10 were capable of catalysing the release of $^3H_2O$ from [1,2-$^3H_2$]GA$_4$ and [2,3-$^3H_2$]GA$_9$. Cultures 27 and 90 were shown to be responsible for this activity. The putative GA 2β-hydroxylase clone was designated as 2B27.

Plasmid DNA, isolated from clone 2B27 using the Promega SV miniprep kit, was sequenced using Amersham's Taq cycle sequencing kit with the M13 universal (−20) and reverse sequencing primers. The chain termination products produced from the sequencing reactions were analysed using an Applied Biosystems 373A automated sequencer. Sequence analysis was performed using the program Sequencer 3.0 from Gene Codes Corporation. Further nucleotide and protein sequence analyses were performed using the University of Wisconsin Genetics Computer Group suite of programs.

Example 2

Assays of GA 2-oxidase Activity

GA 2β-hydroxylase activity was determined by measuring the release of $3H_2O$ from a 2β tritiated GA substrate, as described by Smith and MacMillan (Smith, V. A., and MacMillan, J. in *J. Plant Growth Regulation* 2 251-264 (1984)). The bacterial lysate (90 μl) was incubated with [1,2-$^3H_2$]GA$_4$ or [2,3-$^3H_2$]GA$_9$ (ca. 50000 dpm), in the presence of 4 mM 2-oxoglutarate, 0.5 mM Fe(II)SO$_4$, 4 MM ascorbate, 4 mM DTT, 1 mg/ml catalase, 2 mg/ml BSA, in a final reaction volume of 100 μl. The mixture was incubated at 30° C. for 60 min. The tritiated GAs were removed by the addition of 1 ml of activated charcoal (5% w/v) and subsequent centrifugation for 5 min in a microfuge. Aliquots (0.5 ml) of the supernatant were mixed with 2 ml scintillation fluid and the radioactivity determined by scintillation counting.

In order to confirm the function of the cDNA expression products, bacterial lysate was incubated with [17-$^{14}$C]GAs in the presence of cofactors, as described above. After the incubation, acetic acid (10 μl) and water at pH 3 (140 μl) were added, and the mixture was centrifuged at 3,000 rpm for 10 min. The supernatant was analysed by HPLC with on-line radiomonitoring and products identified by GC-MS, as described previously (MacMillan et al *Plant Physiol.* 113 1369-1377 (1997)).

Example 3

Cloning of cDNAs Encoding GA 2-oxidase from *Arabidopsis thaliana*

The predicted protein sequence of clone 2B27 was used to search the Genomic Survey Sequences database at the National Centre for Biological Information (ncbi.nlm.nih-.gov) using the TblastN program. Two *Arabidopsis* genomic sequences, T3M9-Sp6 and T24E24TF, demonstrated high amino acid sequence identity with the 2B27 sequence. Oligonucleotide primers were designed based on the T3M9-Sp6 genomic sequences:

```
                                    (SEQ ID NO:11)
5'-TAATCACTATCCACCATGTC-3'          (sense), (SEQ ID NO:12)
5'-TGGAGAGAGTCACCCACGTT             (antisense), (SEQ ID NO:13)
5'-GGTTATGACTAACGGGAGGT-3'          (sense), (SEQ ID NO:14)
5'-CTTGTAAGCAGAAGATTTGT-3'          (antisense),
``` and used in PCR reactions with *Arabidopsis* genomic DNA as a template. The PCR reactions consisted of 200 ng of genomic DNA, 1×PCR buffer, 1.5 mM MgCl$_2$, 200 μM deoxynucleoside triphosphates, 1 μM of each primer and 2 units of Taq DNA polymerase (Promega). The reactions were heated to 94° C. for 3 min then 35 cycles of amplification were performed (94° C. for 30 seconds, 55° C. for 30 seconds and 72° C. for 30 seconds) followed by a final 10 min incubation at 72° C. Resulting PCR products were cloned directly into the pCR2.1 vector using the TA cloning kit (Invitrogen) and sequenced as described above. The clones were designated as AtT3 and AtT24. Siliques, flowers, upper stems (the top 2 cm of stem), lower stems, leaves (cauline and rosette) and roots of the Columbia ecotype were collected and frozen in liquid $N_2$. Poly(A)$^+$ mRNA was extracted as described above. Northern blots were prepared by the electrophoresis of 5 μg samples of the poly(A)$^+$ mRNA through agarose gels containing formaldehyde and subsequent transfer to nitrocellulose (Sarnbrook et al *Molecular Cloning: A Laboratory Manual*. Cold Spring Harbor Laboratory Press, Plainview, N.Y. (1989)). Random-primed $^{32}$P-labelled probes were generated for AtT3 and AtT24 using Ready to go labelling beads (Pharmacia). FIG. 3 shows the DNA probe sequences for *A. thaliana* probe T3 (FIG. 3a) and probe T24 (FIG. 3b). Hybridisations were carried out in the presence of 50% formamide at 42° C. for 16 h (hybridisation buffer: 5×SSPE, 2× Denhardts, 0.5% (w/v) SDS, 100 μg/ml denatured sonicated salmon sperm DNA, 10% Dextran sulphate). Blots were washed twice for 10 min in 1×SSC/0.5% SDS at 20° C. A further 2×10 min washes were performed in 0.1×SSC/0.5% SDS at 60° C. Blots were exposed to Kodak MS film at −80° C. with MS intensifying screens: highest expression of both genes was detected in the inflorescence. A cDNA library was constructed using 5 μg of inflorescence poly(A)$^+$ mRNA as described above. A total of 5×10$^5$ recombinant phage in *E. coli* XL1-Blue MRF' were plated on five 24 cm×24 cm square plates. Plaques were grown until confluency (8-10 h), then duplicate lifts were taken on 20×22 cm supported nitrocellulose filters (Nitropure, MSI) and processed as described by Sambrook et al (*Molecular Cloning: A Laboratory Manual*, Cold Spring Harbor Laboratory Press, Plainview, N.Y. (1989)). Hydridization of $^{32}$P-labelled AtT3 and AtT24 probes was performed as described above. Positive plaques were identified by autoradiography and cored from the plates into 750 μl of SM buffer (50 mM Tris HCl pH7.5, 100 mM NaCl, 10 mM MgSO$_4$, 0.5% gelatine) and rescreened until plaque-pure clones were isolated. Plasmid rescue was performed using Stratagene's Rapid Excision kit. The cDNA clones were sequenced and recombinant protein expressed in *E. coli* and tested for GA 2-oxidase activity as described above. The partial nucleotide and deduced amino acid sequences for the clones are shown in FIGS. 5,6,7 and 8.

A third *Arabidopsis* genomic sequence T31E10.11 (AtGA2ox3), with a high amino acid identity with the *P. coccineus* GA 2-oxidase (PcGA2ox1) was also detected in the GenBank database. Its derived amino acid sequence has 53%, 49% and 67% identity (67%, 67% and 84% similarity) with the *P. coccineus* GA 2-oxidase (PcGA2ox1), T3 (AtGA2ox1), and T24 (AtGA2ox2), respectively. The nucleotide sequence of T31 is shown in FIG. 9 and the deduced amino acid sequence is shown in FIG. 10.

Example 4

Transformation of *Arabidopsis* with Sense and Antisense GA 2-oxidase cDNA Constructs The predicted coding region of 2B27 was amplified by PCR using oligonucleotide primers:

```
                                            (SEQ ID NO:15)
5'-TGAGCTCAACCATGGTTGTTCTGTCTCAGC-3'        (sense),
and (SEQ ID NO:16)
5'-TGAGCTCTTAATCAGCAGCAGATTTCTGG-3'         (antisense),
``` each of which had a SacI restriction site incorporated at its 5' end. The PCR product was sub-cloned into pCR2.1 to facilitate DNA sequencing as described previously. The 2B27 coding region was digested with SacI and sub-cloned into SacI site of the binary vector pLARS120, a modified version of pGPTV-Kan (Becker et al. *Plant Mol Biol* 20 1195-1197 (1992)) in which the β-glucuronidase reporter gene is replaced by the cauliflower mosaic virus 35S promoter from pBI220 (Jefferson, R. A., *Plant Mol Biol Rep* 5 387405 (1987)). The DNA was inserted in the sense orientation under the control of the $^{35}$S promoter. The plasmid was introduced into *Agrobacterium tumefaciens* by electroporation and then transferred into *Arabidopsis* cv. Columbia via a vacuum infiltration method (Bechtold et al. *Compt. Rend. Acad. Sci. Serie iii-Sciences de la Vie-Life Science* 316 1194-1199 (1993)). Similarly, SacI fragments of AtT3 and AtT24were sub-cloned into pLARS120, except in these two cases the DNA was inserted in the antisense orientation under the control of the 35S promoter. *Arabidopsis* was transformed with these two antisense constructs as described above.

Example 5(a)

Altered Expression of GA 2-oxidase in Transgenic Plants

The *P. coccineus* 2-oxidase cDNA in sense orientation (PcGA2ox1) and the *A. thaliana* 2-oxidase cDNA in antisense orientations were inserted between the CaMV 35S promoter and nos terminator in the vector pLARS120. The vector pLARS120 is a binary vector for *Agrobacterium*-mediated plant transformation: the T-DNA contains, in addition to the CaMV $^{35}$S promoter and nos terminator, an nptII selectable marker under the nos promoter. The vector is derived from pGPTV-Kan (Becker et al *Plant Mol. Biol.* 20 1195-1197 (1992)), the uidA reporter gene in pGPTV-Kan being replaced by the 35S promoter. The binary expression constructs were introduced into *Agrobacterium tumefaciens* strain GV3101 carrying the pAD1289 plasmid conferring overexpression of VirG by electroporation. These were introduced into *Arabidopsis* by the vacuum infiltration method (Bechtold et al *Compt. Rend. Acad. Sci. Serie iii-Sciences de la Vie-Life Science* 316 1194-1199 (1993)). To identify transgenic plants, seeds from infiltrated plants were grown on MS plates supplemented with kanamycin (50 μg/ml) for approximately 14 days and resistant plants were transferred to compost. T-DNA containing the *P. coccineus* 2-oxidase construct was also introduced into *Nicotiana sylvestris* by the infection of leaf discs with transformed *Agrobacterium tumefaciens*.

Figure 11:
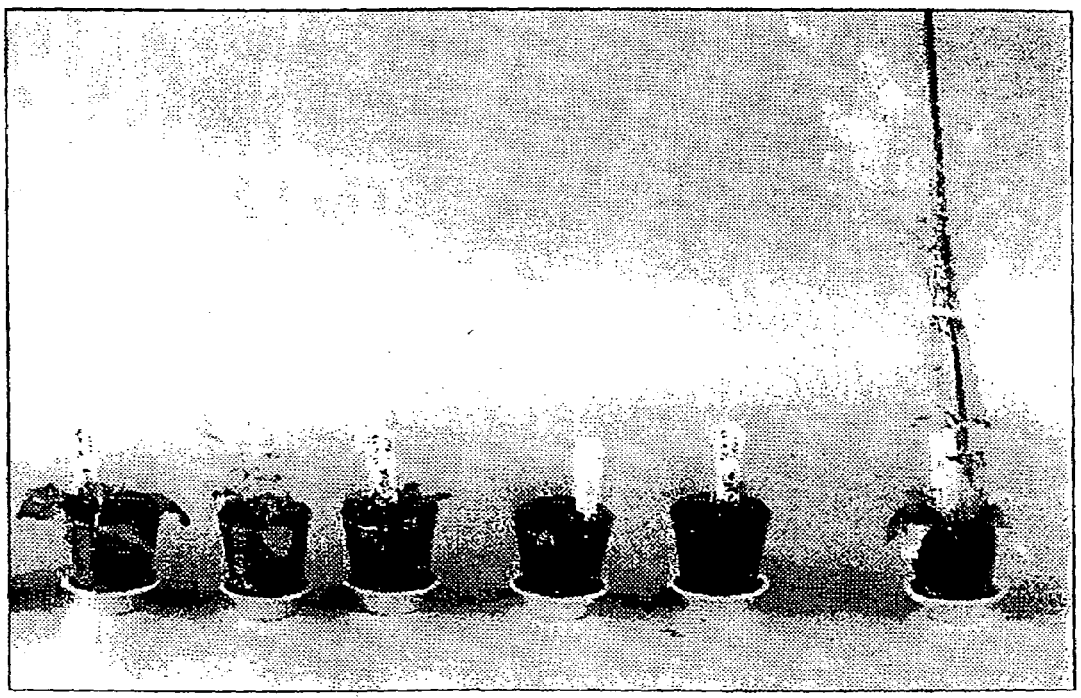
FIG. 11 shows a photograph of transformed *Arabidopsis* plants (Columbia ecotype) expressing *P. coccineus* GA 2-oxidase cDNA under control of CaMV 35S promoter, including a transformed plant showing no phenotype (extreme right).

The transformation of *Arabidopsis* plants with *P. coccineus* GA 2-oxidase cDNA under the control of the CaMV $^{35}$S promoter yielded the following results. Over half of all transformants examined showed some degree of dwarfing, many were severely dwarfed and some failed to bolt. FIG. 11 shows a photograph of a selection of dwarf transformed plants compared with a transformed plant showing no phenotype (Columbia ecotype). The transformants responded to treatment with $GA_3$ with increased stem elongation and normal flower development so that it was possible to obtain seeds. Overexpression of the *P. coccineus* GA 2-oxidase cDNA in *Nicotiana sylvestris* resulted in plants with reduced stem height. One transformant did not bolt or produce flowers, whereas non-transformed plants of the same age had already flowered.

Example 5(b)

Altered Expression of GA 2-oxidase in Transgenic Plants

Five *Arabidopsis* lines that are homozygous for the 35S-PcGA2ox1 transgene were obtained. One line bolted at the same time as wild-type (Columbia) plants but had reduced stem height, whereas the other four lines remained as rosettes and did not bolt when grown in long (16 hour) or short (10 hour) photoperiods. One severely dwarfed line has failed to produce homozygous plants, even when seeds were germinated in the presence of $GA_3$, indicating that seed development was impaired in this line when two copies of the gene were present. The severely dwarfed lines possessed small, dark leaves that remained close to coil level. They produced flower buds when grown in long photoperiods although the flowers did not develop normally and were infertile. No flower buds were obtained when plants were grown in short photoperiods. Treatment of the transgenic lines with 10 μM $GA_3$ enabled them to bolt and produce normal flowers that set viable seed.

Metabolism of $C_{19}$-Gas was compared in a severely dwarfed 35A-PcGA2ox1 line with that in wild-type plants. On the basis of HPLC, the dwarf line converted $GA_1$, $GA_4$, $GA_9$ and $GA_{20}$ to 2-oxidised products to a much greater extent than did the wild-type. The dwarf line did not metabolise $GA_3$, confirming results with recombinant enzyme indicating that $GA_3$ is not a substrate for the GA 2-oxidases. Therefore, this GA can be used, when required, to reverse the GA-deficiency resulting from overexpressing GA 2-oxidase genes.

Northern blot analysis of the 35S-PcGA2ox1 lines confirmed high levels of expression of the transgene. Transcript abundance for GA 20-oxidase (AtGA2ox1) and 3β-hydroxylase (AtGA3ox1) genes was elevated in rosettes of the 35S-PcGA2ox1 lines compared with wild-type plants, whereas native GA 2-oxidase (AtGA2ox2) transcript level was reduced, as a consequence of the control mechanisms for GA homeostasis.

Example 6

Expression Patterns of *Arabidopsis* GA 2-oxidase Genes T3 and T24 (AtGA2ox1 and AtGA2ox2 Respectively)

The expression patterns of *Arabidopsis* GA 2-oxidase genes T3 and T24 were examined by probing Northern blots of RNA extracted from different tissues with the full length cDNAs. The genes showed similar patterns of expression, with transcript for both genes present in leaves, lower stems, upper stems, flowers and siliques. The highest levels of expression were in flowers, siliques and upper stems in decreasing order of transcript abundance. T24, but not T3, was also expressed in roots. Transcript abundance for both T3 and T24 in immature flower buds and pedicels of the GA-deficient *Arabidopsis* mutant, ga1-2, is increased after treatment with $GA_3$, indicating that expression of these 2-oxidase genes is upregulated by GA. This contrasts with expression of the GA 20-oxidase and 3β-hydroxylase genes which are downregulated by GA. Transcript abundance for T31 was much lower in all tissues than for T3 or T14. T31 transcript was detected by RT-PCR in flowers, upper stems and leaves but not in roots or siliques.

Example 7

Function of the Recombinant GA 2-oxidases from *Phaseolus coccineus* and *Arabidopsis thaliana*

The catalytic properties of the recombinant proteins obtained by expressing the cDNAs from *P. coccineus* (PcGA2ox1) and *A. thaliana* (AtGA2ox1, AtGA2ox2 and AtGa2ox3) in *E. coli* were examined by incubating in the presence of dioxygenase cofactors with a range of $^{14}C$-labelled GA substrates, consisting of the $C_{19}$-GAs $GA_1$, $GA_4$, $GA_9$ and $GA_{20}$, and the $C_{20}$-GAs, $GA_{12}$ and $GA_{15}$. This last compound was incubated in both its closed and open lactone forms. No conversion of $GA_{12}$ was obtained with any of the enzymes, whereas $GA_{15}$ was converted to a single product by PcGA2ox1 and AtGA2ox2. The open lactone form of $GA_{15}$ (20-hydroxy$GA_{12}$) was converted to the same product by AtGAox2, but less efficiently than was the lactone form, whereas there was no conversion of $GA_{15}$ open lactone by PcGA2ox1. The mass spectrum of the product from $GA_{15}$ is consistent with it being 2β-hydroxy$GA_{15}$, although, because the authentic compound is not available for comparison, the identity of this product is tentative.

Comparison of the substrate specificities of the recombinant enzymes for the $C_{19}$-GAs (Table 1) indicated that $GA_9$ was the preferred substrate for PcGA2ox1, AtGA2ox1 and AtGA2ox2. The recombinant enzymes differed somewhat in their substrate specificities, with $GA_4$ being converted as effectively as $GA_9$ by PcGA2ox1 and AtGA2ox3, but a relatively poor substrate for AtGA2ox1 and AtGA2ox2. Although $GA_{20}$ was 2β-hydroxylated more efficiently than $GA_4$ by AtGA2ox1 and AtGA2ox2, no $GA_{29}$ catabolite was detected after incubations with $GA_{20}$, whereas low yields of $GA_{34}$ catabolite were obtained when $GA_4$ was incubated with PcGA2ox1, AtGA2ox2 and AtGA2ox3. The activities of recombinant PcGA2ox1, AtGA2ox2 and AtGA2ox3 for 2β-hydroxylation of $GA_9$ varied little between pH 6.5 and 8, and that of AtGA2ox1 peaked at pH 7 with no detectable activity at pH $\leq 5.9$ and $\geq 8.1$.

The results indicate that the non-3β-hydroxy $C_{19}$-GAs, which are immediate precursors of the biologically active compounds, are better substrates for the GA 2-oxidases than are the active Gas themselves. Therefore, overexpression of GA 2-oxidase genes would result in very little active GA being produced.

TABLE 1

Specificity of recombinant GA 2-oxidase for $C_{19}$-GA substrates

| Recombinant Enzymes | $^{14}C$-labelled GA substrate | 2β-Hydroxy GA product | GA-catabolite Product |
| --- | --- | --- | --- |
| PcGA2ox1 | $GA_1$ | 100 | — |
|  | $GA_4$ | 83 | 17 |
|  | $GA_9$ | 87 | 13 |
|  | $GA_{20}$ | 86 | — |

TABLE 1-continued

Specificity of recombinant GA 2-oxidase for $C_{19}$-GA substrates

| Recombinant Enzymes | $^{14}$C-labelled GA substrate | 2β-Hydroxy GA product | GA-catabolite Product |
|---|---|---|---|
| AtGA2ox1 | $GA_1$ | 41 | — |
|  | $GA_4$ | 25 | — |
|  | $GA_9$ | 91 | — |
|  | $GA_{20}$ | 50 | — |
| AtGA2ox2 | $GA_1$ | 100 | — |
|  | $GA_4$ | 77 | 23 |
|  | $GA_9$ | — | 100 |
|  | $GA_{20}$ | 100 | — |
| AtGA2ox3 | $GA_1$ | 100 | Trace |
|  | $GA_4$ | 86 | 14 |
|  | $GA_9$ | 100 | — |
|  | $GA_{20}$ | 25 | — |

Values are % yield by HPLC-radiomonitoring of products after incubation of cell lysates from *E. coli* expressing the cDNA with $^{14}$C-labelled GA substrate and cofactors for 2.5 h. Products and substrate were separated by HPLC and products identified by GC-MS. Where combined yield of products <100%, the remainder is unconverted substrate.

Gibberellin (GA) Biosynthesis

FIG. 4 shows the two major pathways of gibberellin (GA) biosynthesis, from $GA_{12}$ to $GA_4$ and from $GA_{53}$ to $GA_1$. $GA_1$ and $GA_4$ are the biologically active GAs. The conversion of $GA_{12}$ to $GA_9$ and of $GA_{53}$ to $GA_{20}$ are catalysed by GA 20-oxidase. The conversion of $GA_9$ to $GA_4$ and of $GA_{20}$ to $GA_1$ are catalysed by GA 3β-hydroxylase. $GA_9$, $GA_4$, $GA_{20}$ and $GA_1$ are all substrates for the 2β-hydroxylase activity of GA 2-oxidase, being converted to $GA_{51}$, $GA_{34}$, $GA_{29}$ and $GA_8$ respectively. These 2β-hydroxylated GAs can be further oxidised to the corresponding catabolites. The present invention shows that the enzyme from *P. coccineus* and the two enzymes from *Arabidopsis thaliana* catalyse the 2β-hydroxylation of each substrate. In addition, the present invention shows that the *P. coccineus* enzyme and one of the *A. thaliana* enzymes forms $GA_{51}$-catabolite and $GA_{34}$-catabolite when incubated with $GA_9$ and $GA_4$ respectively.

What is claimed is:

1. A plant cell transformed with a vector comprising a nucleic acid molecule operatively linked to a promoter, wherein the nucleic acid molecule encodes a polypeptide having gibberellin 2-oxidase enzyme activity, and wherein said nucleic acid molecule hybridizes to the complement of the coding region of SEQ ID NO:1 under stringent conditions that comprise hybridization at 65° C. and washing in 0.1× SSC/0.1% SDS at 68° C.

2. The plant cell of claim 1, wherein said polypeptide is a gibberellin 2-oxidase enzyme from *Phaseolus* or *Arabidopsis*.

3. The plant cell of claim 2, wherein said polypeptide is a gibberellin 2-oxidase enzyme from *Phaseolus coccineus* or *Arabidopsis thaliana*.

4. The plant cell of claim 1, wherein said nucleic acid molecule comprises nucleotides 68 to 1063 of SEQ ID NO:1.

5. The plant cell of claim 4, wherein said nucleic acid molecule comprises SEQ ID NO: 1.

6. The plant cell of claim 1, wherein said nucleic acid molecule encodes a polypeptide with an amino acid sequence consisting essentially of SEQ ID NO:2.

7. The plant cell of claim 1, wherein said promoter is a constitutive promoter.

8. The plant cell of claim 1, wherein said promoter is specific for expression in a particular plant cell.

9. The plant cell of claim 1, wherein said expression of said polypeptide having the activity of a gibberellin 2-oxidase enzyme results in a reduced concentration of bioactive gibberellins in a plant grown from said plant cell.

10. The plant cell of claim 1, wherein said polypeptide catalyses the 2β-oxidation of a $C_{19}$-gibberellin molecule to introduce a hydroxyl group at C-2.

11. The plant cell of claim 10, wherein said polypeptide further catalyses the oxidation of the hydroxyl group introduced at C-2 to yield the ketone derivative.

12. The plant cell of claim 1, wherein said inhibition of plant growth reduces bolting in a plant grown from said plant cell.

13. A transgenic plant or part thereof comprising the transformed plant cell of claim 1.

14. A plant material capable of proliferation, obtained from the plant of claim 13, wherein said plant material capable of proliferation comprises said transformed plant cell.

15. A plant material comprising said transformed plant cell, as claimed in claim 14 which is selected from the group consisting of protoplasts, cells, calli, tissues, organs, seeds, embryos, egg cells, and zygotes.

16. A plant comprising the plant cell of any one of claims 1-6 and 7-12, wherein the plant has a reduced height and a delayed or absent inflorescence development as compared to a non-transformed plant and wherein application of $GA_3$ to said plant produces a plant with increased stem elongation and normal flower development.

17. The transgenic plant of claim 13, wherein the plant has a reduced height and a delayed or absent inflorescence development as compared to a non-transformed plant and wherein application of $GA_3$ to said plant produces a plant with increased stem elongation and normal flower development.

18. The plant material of any one of claims 14 and 15, wherein a plant grown from said plant material has a reduced height and a delayed or absent inflorescence development as compared to a non-transformed plant and wherein application of $GA_3$ to said plant produces a plant with increased stem elongation and normal flower development.

* * * * *

SEQUENCE LISTING

<160> NUMBER OF SEQ ID NOS: 16

<210> SEQ ID NO 1
<211> LENGTH: 1318
<212> TYPE: DNA
<213> ORGANISM: Phaseolus coccineus

<400> SEQUENCE: 1

```
gtttctcttc cttaccctgt tctgcttctc tttttcatag taacaatcga caacaacaac      60
aacaaccatg gttgttctgt ctcagccagc attgaaccag ttttccttc tgaaaccatt     120 caagtccacg cccttgttca cggggattcc tgtggtcgac ctcacgcacc ccgatgccaa     180
gaatctcata gtgaacgcct gtagggactt cggcttcttc aagcttgtga accatggtgt     240
tccattggag ttaatggcca atttagaaaa cgaggccctc aggttctta aaaaatctca     300 gtccgagaaa gacagagctg gtcccccga ccctttcggc tatggtagca agaggattgg     360
cccaaacggt gatgtcggtt gggtcgaata cctcctcctc aacaccaacc ctgatgttat     420
ctcacccaaa tcactttgca ttttccgaga aaatcctcat catttcaggg cggtggtgga     480
gaactacatt acagcagtga agaacatgtg ctatgcggtg ttggaattga tggcggaggg     540
gttggggata aggcagagga atacgttaag caggttgctg aaggatgaga aaagtgattc     600
gtgcttcagg ttgaaccact acccgccttg ccctgaggtg caagcactga accggaattt     660
ggttgggttt ggggagcaca cagacccaca gataatttct gtcttaagat ctaacagcac     720
atctggcttg caaatctgtc tcacagatgg cacttgggtt tcagtcccac ctgatcagac     780
ttcctttttc atcaatgttg gtgacgctct acaggtaatg actaatggga ggtttaaaag     840
tgtaaagcat agggttttgg ctgacacaac gaagtcaagg ttatcaatga tctactttgg     900
aggaccagcg ttgagtgaaa atatagcacc tttaccttca gtgatgttaa aaggagagga     960
gtgtttgtac aaagagttca catggtgtga atacaagaag gctgcgtaca cttcaaggct    1020
```

-continued

```
agctgataat aggcttgccc ctttccagaa atctgctgct gattaaccaa acacaccctt    1080
caaattccac tcattttacg cacgtgttat taccccaatt ttctttcctt tttcttttcc    1140
tgtgtctgtc taggtttcaa acagttgact ctacttgaca tatatagaaa atgaataggt    1200
taagatgttt atcattttct ttttcttgtt tcatctaagt gtaacagttg gtctcaactt    1260
ccctttcctc aattgtcaat ggaacgcaac tctagttaca aaaaaaaaaa aaaaaaa      1318
```

<210> SEQ ID NO 2
<211> LENGTH: 331
<212> TYPE: PRT
<213> ORGANISM: Phaseolus coccineus

<400> SEQUENCE: 2

```
Met Val Val Leu Ser Gln Pro Ala Leu Asn Gln Phe Phe Leu Leu Lys
  1               5                  10                  15

Pro Phe Lys Ser Thr Pro Leu Phe Thr Gly Ile Pro Val Val Asp Leu
             20                  25                  30

Thr His Pro Asp Ala Lys Asn Leu Ile Val Asn Ala Cys Arg Asp Phe
         35                  40                  45

Gly Phe Phe Lys Leu Val Asn His Gly Val Pro Leu Glu Leu Met Ala
     50                  55                  60

Asn Leu Glu Asn Glu Ala Leu Arg Phe Phe Lys Lys Ser Gln Ser Glu
 65                  70                  75                  80

Lys Asp Arg Ala Gly Pro Pro Asp Pro Phe Gly Tyr Gly Ser Lys Arg
                 85                  90                  95

Ile Gly Pro Asn Gly Asp Val Gly Trp Val Glu Tyr Leu Leu Leu Asn
            100                 105                 110

Thr Asn Pro Asp Val Ile Ser Pro Lys Ser Leu Cys Ile Phe Arg Glu
        115                 120                 125

Asn Pro His His Phe Arg Ala Val Val Glu Asn Tyr Ile Thr Ala Val
    130                 135                 140

Lys Asn Met Cys Tyr Ala Val Leu Glu Leu Met Ala Glu Gly Leu Gly
145                 150                 155                 160

Ile Arg Gln Arg Asn Thr Leu Ser Arg Leu Leu Lys Asp Glu Lys Ser
                165                 170                 175

Asp Ser Cys Phe Arg Leu Asn His Tyr Pro Pro Cys Pro Glu Val Gln
            180                 185                 190

Ala Leu Asn Arg Asn Leu Val Gly Phe Gly Glu His Thr Asp Pro Gln
        195                 200                 205

Ile Ile Ser Val Leu Arg Ser Asn Ser Thr Ser Gly Leu Gln Ile Cys
    210                 215                 220

Leu Thr Asp Gly Thr Trp Val Ser Val Pro Pro Asp Gln Thr Ser Phe
225                 230                 235                 240

Phe Ile Asn Val Gly Asp Ala Leu Gln Val Met Thr Asn Gly Arg Phe
                245                 250                 255

Lys Ser Val Lys His Arg Val Leu Ala Asp Thr Thr Lys Ser Arg Leu
            260                 265                 270

Ser Met Ile Tyr Phe Gly Gly Pro Ala Leu Ser Glu Asn Ile Ala Pro
        275                 280                 285

Leu Pro Ser Val Met Leu Lys Gly Glu Glu Cys Leu Tyr Lys Glu Phe
    290                 295                 300

Thr Trp Cys Glu Tyr Lys Lys Ala Ala Tyr Thr Ser Arg Leu Ala Asp
305                 310                 315                 320

Asn Arg Leu Ala Pro Phe Gln Lys Ser Ala Ala
                325                 330
```

<210> SEQ ID NO 3
<211> LENGTH: 210
<212> TYPE: DNA
<213> ORGANISM: Artificial Sequence
<220> FEATURE:
<223> OTHER INFORMATION: Description of Artificial Sequence: Probe

<400> SEQUENCE: 3

```
taatcactat ccaccatgtc ctcttagcaa taagaaaacc aatggtggta agaatgtgat      60
tggttttggt gaacacacag atcctcaaat catctctgtc ttaagatcta acaacacttc     120
tggtctccaa attaatctaa atgatggctc atggatctct gtccctcccg atcacacttc     180
cttcttcttc aacgtgggtg actctctcca                                      210
```

<210> SEQ ID NO 4
<211> LENGTH: 199
<212> TYPE: DNA
<213> ORGANISM: Artificial Sequence
<220> FEATURE:
<223> OTHER INFORMATION: Description of Artificial Sequence: Probe

<400> SEQUENCE: 4

```
ggttatgact aacgggaggt tcaagagtgt taaacacagg gtcttagccg atacaaggag      60
atcgaggatt tcaatgatat atttcggcgg accgccattg agccagaaga tcgcaccatt     120
gccatgcctt gtccctgagc aagatgattg gctttacaaa gaattcactt ggtctcaata     180
caaatcttct gcttacaag                                                  199
```

<210> SEQ ID NO 5
<211> LENGTH: 1318
<212> TYPE: DNA
<213> ORGANISM: Arabidopsis thaliana
<220> FEATURE:
<221> NAME/KEY: misc_feature
<222> LOCATION: (1243, 1265)
<223> OTHER INFORMATION: unidentified residue

<400> SEQUENCE: 5

```
tcaaatcaa aaaattcta tcaaacaagg aaatatatca atggcggtat tgtctaaacc        60
ggtagcaata ccaaaatccg ggttctctct aatcccggtt atagatatgt ctgacccaga     120
atccaaacat gccctcgtga aagcatgcga agacttcggc ttcttcaagg tgatcaacca     180
tggcgtttcc gcagagctag tctctgtttt agaacacagg accgtcgatt tcttctcgtt     240
gcccaagtca gagaaaaccc aagtcgcagg ttatcccttc ggatacggga acagtaagat     300
tggtcggaat ggtgacgtgg gttgggttga gtacttgttg atgaacgcta atcatgattc     360
cggttcgggt ccactatttc caagtcttct caaaagcccg gaactttca  gaaacgcatt     420
ggaagagtac acaacatcag tgagaaaaat gacattcgat gttttggaga gatcacaga     480
tgggctaggg atcaaaccga ggaacacact tagcaagctt gtgtctgacc aaaacacgga     540
ctcgatattg agacttaatc actatccacc atgtcctctt agcaataaga aaccaatgg     600
tggtaagaat gtgattggtt ttggtgaaca cacagatcct caaatcatct ctgtcttaag     660
atctaacaac acttctggtc tccaaattaa tctaaatgat ggctcatgga tctctgtccc     720
tcccgatcac acttccttct tcttcaacgt tggtgactct ctccaggtga tgacaaatgg     780
gaggttcaag agcgtgaggc ataggggtttt agctaactgt aaaaaatcta gggtttctat     840
gatttacttc gctggacctt cattgactca gagaatcgct ccgttgacat gtttgataga     900
```

```
caatgaggac gagaggttgt acgaggagtt tacttggtct gaatacaaaa actctaccta      960
caactctaga ttgtctgata ataggcttca acaattcgaa aggaagacta taaaaaatct     1020
cctaaattga tgtgatatat ctatttaatc tataagtgtg tgctacatac agacaatgca     1080
tctgtatatt ttgaagtata atgttatttg ttaatccaat aactgtaaaa acatgcaaga     1140
gtgtgtttgt tgtttcgta atatcaacat cgctcccatc ttttatggat aaaaaaaaa      1200 aaaaaaaaaa cactgttttg atgtaagcta cattttactt tangtgtaca tcttattgtg     1260
ttaantaaat tatttcaaaa taaaaaaaaa aaaaaaaaaa aaaaaaaaaa aaaaaaa       1318
```

<210> SEQ ID NO 6
<211> LENGTH: 329
<212> TYPE: PRT
<213> ORGANISM: Arabidopsis thaliana

<400> SEQUENCE: 6

```
Met Ala Val Leu Ser Lys Pro Val Ala Ile Pro Lys Ser Gly Phe Ser
 1               5                  10                  15

Leu Ile Pro Val Ile Asp Met Ser Asp Pro Glu Ser Lys His Ala Leu
            20                  25                  30

Val Lys Ala Cys Glu Asp Phe Gly Phe Phe Lys Val Ile Asn His Gly
        35                  40                  45

Val Ser Ala Glu Leu Val Ser Val Leu Glu His Glu Thr Val Asp Phe
    50                  55                  60

Phe Ser Leu Pro Lys Ser Glu Lys Thr Gln Val Ala Gly Tyr Pro Phe
65                  70                  75                  80

Gly Tyr Gly Asn Ser Lys Ile Gly Arg Asn Gly Asp Val Gly Trp Val
                85                  90                  95

Glu Tyr Leu Leu Met Asn Ala Asn His Asp Ser Gly Ser Gly Pro Leu
           100                 105                 110

Phe Pro Ser Leu Leu Lys Ser Pro Gly Thr Phe Arg Asn Ala Leu Glu
       115                 120                 125

Glu Tyr Thr Thr Ser Val Arg Lys Met Thr Phe Asp Val Leu Glu Lys
   130                 135                 140

Ile Thr Asp Gly Leu Gly Ile Lys Pro Arg Asn Thr Leu Ser Lys Leu
145                 150                 155                 160

Val Ser Asp Gln Asn Thr Asp Ser Ile Leu Arg Leu Asn His Tyr Pro
                165                 170                 175

Pro Cys Pro Leu Ser Asn Lys Lys Thr Asn Gly Gly Lys Asn Val Ile
            180                 185                 190

Gly Phe Gly Glu His Thr Asp Pro Gln Ile Ile Ser Val Leu Arg Ser
        195                 200                 205

Asn Asn Thr Ser Gly Leu Gln Ile Asn Leu Asn Asp Gly Ser Trp Ile
    210                 215                 220

Ser Val Pro Pro Asp His Thr Ser Phe Phe Asn Val Gly Asp Ser
225                 230                 235                 240

Leu Gln Val Met Thr Asn Gly Arg Phe Lys Ser Val Arg His Arg Val
                245                 250                 255

Leu Ala Asn Cys Lys Lys Ser Arg Val Ser Met Ile Tyr Phe Ala Gly
            260                 265                 270

Pro Ser Leu Thr Gln Arg Ile Ala Pro Leu Thr Cys Leu Ile Asp Asn
        275                 280                 285

Glu Asp Glu Arg Leu Tyr Glu Glu Phe Thr Trp Ser Glu Tyr Lys Asn
    290                 295                 300
```

Ser Thr Tyr Asn Ser Arg Leu Ser Asp Asn Arg Leu Gln Gln Phe Glu
305                 310                 315                 320

Arg Lys Thr Ile Lys Asn Leu Leu Asn
                325

<210> SEQ ID NO 7
<211> LENGTH: 1237
<212> TYPE: DNA
<213> ORGANISM: Arabidopsis thaliana

<400> SEQUENCE: 7

| | | | | | |
|---|---|---|---|---|---|
| gaattcggca | cgagtttcct | tcttcttcct | caacctttgc | ttcaatcttc | aacaactttc | 60 |
| tttttataaa | gattttgcaa | gttaagtgta | aacctacaaa | aaccaaacat | ggtggttttg | 120 |
| ccacagccag | tcactttaga | taaccacatc | tccctaatcc | ccacatacaa | accggttccg | 180 |
| gttctcactt | cccattcaat | ccccgtcgtc | aacctagccg | atccggaagc | gaaaacccga | 240 |
| atcgtaaaag | cctgcgagga | gttcgggttc | ttcaaggtcg | taaccacgg | agtccgaccc | 300 |
| gaactcatga | ctcggttaga | gcaggaggct | attggcttct | tcggcttgcc | tcagtctctt | 360 |
| aaaaaccggg | ccggtccacc | tgaaccgtac | ggttatggta | taaacggat | tggaccaaac | 420 |
| ggtgacgttg | gttggattga | gtatctcctc | ctcaatgcta | atcctcagct | ctcctctcct | 480 |
| aaaacctccg | ccgttttccg | tcaaaccct | caaattttcc | gtgagtcggt | ggaggagtac | 540 |
| atgaaggaga | ttaaggaagt | gtcgtacaag | gtgttggaga | tggttgccga | gaactaggg | 600 |
| atagagccaa | gggacactct | gagtaaaatg | ctgagagatg | agaagagtga | ctcgtgcctg | 660 |
| agactaaacc | attatccggc | ggcggaggaa | gaggcggaga | agatggtgaa | ggtggggttt | 720 |
| ggggaacaca | cagacccaca | gataatctca | gtgctaagat | ctaataacac | ggcgggtctt | 780 |
| caaatctgtg | tgaaagatgg | aagttgggtc | gctgtccctc | ctgatcactc | ttctttcttc | 840 |
| attaatgttg | gagatgctct | tcaggttatg | actaacggga | ggttcaagag | tgttaaacac | 900 |
| agggtcttag | ccgatacaag | gagatcgagg | atttcaatga | tatatttcgg | cggaccgcca | 960 |
| ttgagccaga | gatcgcacc | attgccatgc | cttgtccctg | agcaagatga | ttggctttac | 1020 |
| aaagaattca | cttggtctca | atacaaatct | tctgcttaca | agtctaagct | tggtgattat | 1080 |
| agacttggtc | tctttgagaa | acaacctctt | ctcaatcata | aaaccttgt | atgagagtag | 1140 |
| tcatgatgat | ctttatcatc | ctttgtacga | tagaaagtca | taatcacaaa | agaaggaaa | 1200 |
| tggatagtgt | tttggattaa | aaaaaaaaa | aaaaaa | | | 1237 |

<210> SEQ ID NO 8
<211> LENGTH: 341
<212> TYPE: PRT
<213> ORGANISM: Arabidopsis thaliana

<400> SEQUENCE: 8

Met Val Val Leu Pro Gln Pro Val Thr Leu Asp Asn His Ile Ser Leu
1               5                   10                  15

Ile Pro Thr Tyr Lys Pro Val Pro Val Leu Thr Ser His Ser Ile Pro
                20                  25                  30

Val Val Asn Leu Ala Asp Pro Glu Ala Lys Thr Arg Ile Val Lys Ala
            35                  40                  45

Cys Glu Glu Phe Gly Phe Phe Lys Val Val Asn His Gly Val Arg Pro
        50                  55                  60

Glu Leu Met Thr Arg Leu Glu Gln Glu Ala Ile Gly Phe Phe Gly Leu
65              70                  75                  80

```
Pro Gln Ser Leu Lys Asn Arg Ala Gly Pro Pro Glu Pro Tyr Gly Tyr
                85                  90                  95
Gly Asn Lys Arg Ile Gly Pro Asn Gly Asp Val Gly Trp Ile Glu Tyr
            100                 105                 110
Leu Leu Leu Asn Ala Asn Pro Gln Leu Ser Ser Pro Lys Thr Ser Ala
        115                 120                 125
Val Phe Arg Gln Thr Pro Gln Ile Phe Arg Glu Ser Val Glu Tyr
    130                 135                 140
Met Lys Glu Ile Lys Glu Val Ser Tyr Lys Val Leu Glu Met Val Ala
145                 150                 155                 160
Glu Glu Leu Gly Ile Glu Pro Arg Asp Thr Leu Ser Lys Met Leu Arg
                165                 170                 175
Asp Glu Lys Ser Asp Ser Cys Leu Arg Leu Asn His Tyr Pro Ala Ala
            180                 185                 190
Glu Glu Glu Ala Glu Lys Met Val Lys Val Gly Phe Gly Glu His Thr
        195                 200                 205
Asp Pro Gln Ile Ile Ser Val Leu Arg Ser Asn Asn Thr Ala Gly Leu
    210                 215                 220
Gln Ile Cys Val Lys Asp Gly Ser Trp Val Ala Val Pro Pro Asp His
225                 230                 235                 240
Ser Ser Phe Phe Ile Asn Val Gly Asp Ala Leu Gln Val Met Thr Asn
                245                 250                 255
Gly Arg Phe Lys Ser Val Lys His Arg Val Leu Ala Asp Thr Arg Arg
            260                 265                 270
Ser Arg Ile Ser Met Ile Tyr Phe Gly Gly Pro Pro Leu Ser Gln Lys
        275                 280                 285
Ile Ala Pro Leu Pro Cys Leu Val Pro Glu Gln Asp Asp Trp Leu Tyr
    290                 295                 300
Lys Glu Phe Thr Trp Ser Gln Tyr Lys Ser Ser Ala Tyr Lys Ser Lys
305                 310                 315                 320
Leu Gly Asp Tyr Arg Leu Gly Leu Phe Glu Lys Gln Pro Leu Leu Asn
                325                 330                 335
His Lys Thr Leu Val
            340

<210> SEQ ID NO 9
<211> LENGTH: 1008
<212> TYPE: DNA
<213> ORGANISM: Arabidopsis thaliana

<400> SEQUENCE: 9
atggtaattg tgttacagcc agccagtttt gatagcaacc tctatgttaa tccaaaatgc      60
aaaccgcgtc cggttttaat ccctgttata gacttaaccg actcagatgc caaacccaa     120 atcgtcaagg catgtgaaga gtttgggttc ttcaaagtca tcaaccatgg ggtccgaccc     180
gatcttttga ctcagttgga gcaagaagcc atcaacttct tgctttgca tcactctctc     240 aaagacaaag cgggtccacc tgaccgtttt ggttacggta ctaaaaggat tggacccaat     300
ggtgaccttg ctggcttgga gtacattctc cttaatgcta atctttgcct tgagtctcac     360
aaaaccaccg ccattttccg gcacaccct gcaattttca gagaggcagt ggaagagtac     420
attaaagaga tgaagagaat gtcgagcaaa tttctggaaa tggtagagga agagctaaag     480
atagagccaa aggagaagct gagccgtttg gtgaaagtga agaaagtga ttcgtgcctg     540 agaatgaacc attacccgga agaggaagag actccggtca aggaagagat tgggttcggt     600
```

-continued

```
gagcacactg atccacagtt gatatcactg ctcagatcaa acgacacaga gggtttgcaa      660
atctgtgtca agatggaac atgggttgat gttacacctg atcactcctc tttcttcgtt       720
cttgtcggag atactcttca ggtgatgaca acggaagat tcaagagtgt gaaacataga      780
gtggtgacaa atacaaagag gtcaaggata tcgatgatct acttcgcagg tcctcctttg     840
agcgagaaga ttgcaccatt atcatgcctt gtgccaaagc aagatgattg cctttataat    900
gagtttactt ggtctcaata caagttatct gcttacaaaa ctaagcttgg tgactatagg    960
cttggtctct ttgagaaacg acctccattt tctctatcca atgtttga                1008
```

<210> SEQ ID NO 10
<211> LENGTH: 335
<212> TYPE: PRT
<213> ORGANISM: Arabidopsis thaliana

<400> SEQUENCE: 10

```
Met Val Ile Val Leu Gln Pro Ala Ser Phe Asp Ser Asn Leu Tyr Val
  1               5                  10                  15

Asn Pro Lys Cys Lys Pro Arg Pro Val Leu Ile Pro Val Ile Asp Leu
                 20                  25                  30

Thr Asp Ser Asp Ala Lys Thr Gln Ile Val Lys Ala Cys Glu Glu Phe
             35                  40                  45

Gly Phe Phe Lys Val Ile Asn His Gly Val Arg Pro Asp Leu Leu Thr
         50                  55                  60

Gln Leu Glu Gln Glu Ala Ile Asn Phe Ala Leu His His Ser Leu
 65                  70                  75                  80

Lys Asp Lys Ala Gly Pro Pro Asp Pro Phe Gly Tyr Gly Thr Lys Arg
                 85                  90                  95

Ile Gly Pro Asn Gly Asp Leu Gly Trp Leu Glu Tyr Ile Leu Leu Asn
            100                 105                 110

Ala Asn Leu Cys Leu Glu Ser His Lys Thr Thr Ala Ile Phe Arg His
        115                 120                 125

Thr Pro Ala Ile Phe Arg Glu Ala Val Glu Glu Tyr Ile Lys Glu Met
130                 135                 140

Lys Arg Met Ser Ser Lys Phe Leu Glu Met Val Glu Glu Leu Lys
145                 150                 155                 160

Ile Glu Pro Lys Glu Lys Leu Ser Arg Leu Val Lys Val Lys Glu Ser
                165                 170                 175

Asp Ser Cys Leu Arg Met Asn His Tyr Pro Glu Lys Glu Thr Pro
            180                 185                 190

Val Lys Glu Glu Ile Gly Phe Gly Glu His Thr Asp Pro Gln Leu Ile
        195                 200                 205

Ser Leu Leu Arg Ser Asn Asp Thr Glu Gly Leu Gln Ile Cys Val Lys
    210                 215                 220

Asp Gly Thr Trp Val Asp Val Thr Pro Asp His Ser Ser Phe Phe Val
225                 230                 235                 240

Leu Val Gly Asp Thr Leu Gln Val Met Thr Asn Gly Arg Phe Lys Ser
                245                 250                 255

Val Lys His Arg Val Val Thr Asn Thr Lys Arg Ser Arg Ile Ser Met
            260                 265                 270

Ile Tyr Phe Ala Gly Pro Pro Leu Ser Glu Lys Ile Ala Pro Leu Ser
        275                 280                 285

Cys Leu Val Pro Lys Gln Asp Cys Leu Tyr Asn Glu Phe Thr Trp
    290                 295                 300
```

Ser Gln Tyr Lys Leu Ser Ala Tyr Lys Thr Lys Leu Gly Asp Tyr Arg
305                 310                 315                 320

Leu Gly Leu Phe Glu Lys Arg Pro Pro Phe Ser Leu Ser Asn Val
                325                 330                 335

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
taatcactat ccaccatgtc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
tggagagagt cacccacgtt                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
ggttatgact aacgggaggt                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
cttgtaagca gaagatttgt                                              20

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
tgagctcaac catggttgtt ctgtctcagc                                   30

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 16
tgagctctta atcagcagca gatttctgg                                    29